(12) United States Patent
Tabata et al.

(10) Patent No.: US 7,036,978 B2
(45) Date of Patent: May 2, 2006

(54) PYROMETER

(75) Inventors: Makoto Tabata, Kyoto (JP); Hiroyuki Ota, Kyoto (JP); Yoshihide Onishi, Kyoto (JP); Toshihiko Ogura, Tsukuba (JP); Tatsuya Sato, Kyoto (JP); Taiga Sato, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 10/311,059

(22) PCT Filed: Jun. 13, 2001

(86) PCT No.: PCT/JP01/05034

§ 371 (c)(1),
(2), (4) Date: Jun. 4, 2003

(87) PCT Pub. No.: WO01/96825

PCT Pub. Date: Dec. 20, 2001

(65) Prior Publication Data

US 2004/0022297 A1 Feb. 5, 2004

(30) Foreign Application Priority Data

Jun. 13, 2000 (JP) .............................. 2000-177407

(51) Int. Cl.
*G01J 5/00* (2006.01)
(52) U.S. Cl. ..................... 374/121; 374/131; 600/474
(58) Field of Classification Search ............... 374/133, 374/169, 121, 1, 131, 134, 120; 600/474; 702/99, 104, 131, 135
See application file for complete search history.

(56) References Cited

U.S. PATENT DOCUMENTS

| 4,602,642 | A | | 7/1986 | O'Hara et al. |
| 5,017,018 | A | | 5/1991 | Iuchi et al. |
| 5,169,235 | A | * | 12/1992 | Tominaga et al. .......... 374/121 |
| 5,232,284 | A | | 8/1993 | Egawa et al. |
| RE34,507 | E | * | 1/1994 | Egawa et al. ............... 374/126 |
| 5,293,877 | A | * | 3/1994 | O'Hara et al. .............. 374/131 |
| 5,368,038 | A | | 11/1994 | Fraden |
| 5,860,741 | A | | 1/1999 | Tsao et al. |
| 6,076,962 | A | | 6/2000 | Chen |
| 6,152,595 | A | | 11/2000 | Beerwerth et al. |
| 6,155,712 | A | * | 12/2000 | Egawa ........................ 374/126 |
| 6,203,193 | B1 | * | 3/2001 | Egawa ........................ 374/126 |
| 6,241,384 | B1 | | 6/2001 | Pompei et al. |
| 6,292,685 | B1 | | 9/2001 | Pompei |
| 6,332,090 | B1 | | 12/2001 | DeFrank et al. |
| 6,357,909 | B1 | * | 3/2002 | Watanabe .................... 374/131 |
| 6,386,757 | B1 | * | 5/2002 | Konno ......................... 374/158 |
| 6,435,711 | B1 | * | 8/2002 | Gerlitz ........................ 374/130 |
| 6,499,877 | B1 | * | 12/2002 | Pompei ........................ 374/133 |

(Continued)

FOREIGN PATENT DOCUMENTS

EP 0 337 724 10/1989

(Continued)

*Primary Examiner*—Diego Gutierrez
*Assistant Examiner*—Mirellys Jagan
(74) *Attorney, Agent, or Firm*—Morrison & Foerster LLP

(57) ABSTRACT

A first thermistor 8 and a second thermistor 9 are arranged forwardly and rearwardly of a thermopile sensor 5. A thermopile chip 55 is arranged and interposed between the first thermistor 8 and an integrated thermistor 57. A sensor cover is mounted in contact with front and side portions of a can portion 59 of a thermopile casing 56. A temperature or a radiant quantity of infrared rays on the front portion of the can portion is estimated from a temperature change of the integrated thermistor per second.

7 Claims, 29 Drawing Sheets

U.S. PATENT DOCUMENTS

| | | |
|---|---|---|
| 6,513,970 B1 * | 2/2003 | Tabata et al. ............... 374/131 |
| 6,522,912 B1 | 2/2003 | Nakatani et al. |
| 6,565,254 B1 | 5/2003 | Sato et al. |
| 6,572,264 B1 * | 6/2003 | Egawa ....................... 374/133 |
| 6,584,426 B1 | 6/2003 | Ota |
| 6,609,824 B1 * | 8/2003 | Sato et al. .................. 374/132 |
| 6,821,016 B1 | 11/2004 | Sato et al. |
| 2002/0181539 A1 * | 12/2002 | Sato et al. .................. 374/121 |
| 2002/0191670 A1 * | 12/2002 | Huang et al. ............... 374/133 |
| 2004/0086022 A1 | 5/2004 | Kraus et al. |
| 2004/0109490 A1 | 6/2004 | Asakura et al. |

FOREIGN PATENT DOCUMENTS

| | | | |
|---|---|---|---|
| JP | 53022486 A | * | 3/1978 |
| JP | 2-35322 | | 2/1990 |
| JP | 2-201229 | | 8/1990 |
| JP | 04299225 | | 10/1992 |
| JP | 5-126647 | | 5/1993 |
| JP | 8-215154 | | 8/1996 |
| JP | 11-76175 | | 3/1999 |
| JP | 11-351968 | | 12/1999 |
| WO | WO 92/11800 | | 7/1992 |

* cited by examiner (a)

(b)

TEMPERATURE TAKEN IN BLACKBODY FURNACE (a)

TEMPERATURE TAKEN FOR HUMAN BODY (b)

EFFECT OF THERMAL CORRECTION FOR INDIVIDUAL HUMAN BODY (c)

EXAMPLE OF MEASUREMENT STANDBY STATE
DISPLAYED ON ORDINARY OCCASION (a)

EXAMPLE OF MEASUREMENT STANDBY STATE DISPLAYED
WHEN BLACKBODY-FURNACE MEASUREMENT MODE IS SELECTED (b)

PYROMETER

TECHNICAL FIELD

The present invention relates to a radiation thermometer for measuring a temperature of an object being measured, by measuring infrared rays irradiated from the object being measured.

BACKGROUND ART

Conventionally, radiation thermometers of this kind calculate a temperature of an object being measured, on the basis of an output of a thermopile and a temperature of a thermopile chip, in accordance with the following formula of principle $$E = L(T_x^4 - T_a^4)$$

where E: energy (output of a thermopile chip) received by the thermopile chip, L: a coefficient, $T_x$: temperature of an object being measured, and $T_a$: temperature of the thermopile chip.

Also, sensors for measuring a radiant quantity of infrared rays include a thermopile sensor generally constructed such that a thermopile chip is bonded to a metallic stem, a window of silicone glass capable of transmitting therethrough infrared rays is provided on a roof panel, and the whole is sealed by a metallic casing.

With a thermometer making use of such thermopile sensor, as disclosed in JP-A-5-203499, a thermistor is bonded to a portion immediately laterally of a thermopile chip in the metallic casing or behind the thermopile chip with the metallic casing therebetween for the purpose of measuring a temperature of the thermopile chip, and a temperature of the thermistor is assumed to be equal to a temperature of the thermopile chip.

Also, the thermopile chip gives and receives energy in the form of infrared rays from all objects, which are disposed in front of the thermopile chip and different in temperature from the thermopile chip, and converts the energy into voltage to output the same.

Accordingly, a measurement of one thermistor is used and made a representative value of the thermopile sensor in the same manner as the above example, assuming that the thermopile sensor is made isothermal and the thermopile casing involves no temperature difference. While JP-A-2-35322 describes an example of measuring a temperature of a wave guide disposed in front of a thermopile sensor, it is premised on the assumption that a thermopile casing itself involves no temperature difference.

With radiation thermometers, in which a probe is inserted into an ear to measure a body temperature by the medium of infrared rays irradiated from an eardrum, however, heat is conducted to respective members, which constitute the probe, from an external auditory canal or the like to generate a temperature distribution on a thermopile sensor itself when the probe is inserted into an ear at the time of measurement of body temperature. Such influences of heat from outside come out markedly, particularly in the case where the probe is inserted into an ear for a long time and the probe is repeatedly inserted into an ear. When a temperature difference is generated in a thermopile sensor itself and a temperature difference is generated between a thermopile casing disposed in front of a thermopile chip and the thermopile chip, the thermopile chip receives infrared rays from the thermopile casing in addition to infrared rays irradiated from an object (eardrum) being measured, whereby there is caused an error that a higher temperature than that of the actual object being measured is measured.

Also, as for the way of conduction of heat from outside, when a human body is an object being measured, an adult and a child are different in size and depth of earhole and in position and area, in which a probe contacts with an external ear, so that the way of conduction of heat to the probe is varied. Accordingly, errors generated are varied in amount depending upon whether an object being measured is an adult and a child. Further, that manner, in which a thermometer is influenced by heat in the case where temperature measurement is made by the use of a blackbody furnace or the like other than a human body for the purpose of proof of accuracy of the thermometer, is quite different from the case where a human body is an object being measured, and errors generated are naturally different in amount from the case where a human body is an object being measured. Accordingly, with thermometers for persons in a wide range, no correct measurement is obtained when differences in objects being measured are neglected and measurement errors caused by influences of heat from outside are uniformly corrected.

The invention has been thought of in order to solve such problems of the conventional art, and has its object to suppress measurement errors caused by influences of heat from outside, thereby enhancing accuracy in temperature measurement.

DISCLOSURE OF INVENTION

In order to solve the above object, the invention provides a radiation thermometer provided with an infrared-ray sensor for measuring a quantity of infrared rays irradiated from an object being measured, sensor-temperature measuring means for measuring a temperature of the infrared-ray sensor, and temperature calculating means for calculating a temperature of the object being measured, on the basis of a quantity of infrared rays irradiated from the object being measured, and a temperature of the infrared-ray sensor; comprising at least a plurality of sensor-temperature measuring means.

With such constitution, a temperature of the infrared-ray sensor can be correctly measured, and so temperature measurement can be enhanced in accuracy. Here, the infrared-ray sensor includes an infrared-ray pyroelectric sensor, a thermistor bolometer, or the like in addition to a thermopile chip or a thermopile sensor, but is not limited to them.

Also, the plurality of sensor-temperature measuring means are preferably arranged in a position to interpose the infrared-ray sensor therebetween.

Also, the infrared-ray sensor may be arranged on or in the vicinity of an extension line, which connects the plurality of sensor-temperature measuring means together.

Also, the invention provides a radiation thermometer provided with an infrared-ray sensor for measuring a quantity of infrared rays irradiated from an object being measured, sensor-temperature measuring means for measuring a temperature of the infrared-ray sensor, and temperature calculating means for calculating a temperature of the object being measured, on the basis of a quantity of infrared rays irradiated from the object being measured, and a temperature of the infrared-ray sensor; comprising an infrared-ray sensor receiving member for receiving the infrared-ray sensor, and wherein the infrared-ray sensor receiving member comprises an object-side portion positioned on a side of the object being measured, relative to the infrared-ray sensor, and the temperature calculating means has the function of calculating a temperature of the object being measured, on the basis of a quantity of infrared rays irradiated from the object being measured, a quantity of infrared rays irradiated from the object-side portion, and a temperature of the infrared-ray sensor.

With such constitution, it is possible to suppress influences of infrared rays irradiated from the object portion, in front of an infrared-ray sensor, thereby enhancing accuracy in temperature measurement.

Also, there is provided temperature-distribution measuring means for measuring a temperature distribution of the object-side portion, and the temperature calculating means has the function of calculating a quantity of infrared rays irradiated from the object-side portion on the basis of the temperature distribution measured by the temperature-distribution measuring means and calculating a temperature of the object being measured, on the basis of the calculated quantity of infrared rays, a quantity of infrared rays irradiated from the object being measured, and a temperature of the infrared-ray sensor.

Also, the temperature-distribution measuring means may be positioned on a side of the object being measured relative to the infrared-ray sensor.

Also, the temperature-distribution measuring means may measure a temperature distribution of the object-side portion on the basis of a changed portion of a temperature of the sensor per unit time.

Also, there is preferably provided isothermal means for uniformizing a temperature distribution of the object-side portion.

With such constitution, the object-side portion is uniformized and a temperature at one point on the object-side portion is measured, whereby it is possible to estimate a temperature of the object-side portion.

Also, the isothermal means may be formed from a substance of high thermal conductivity and contacts with the object-side portion to cover at least a part thereof.

Also, it is preferable that the object-side portion of the infrared-ray sensor receiving member comprise an infrared-ray transmitting portion for transmitting therethrough infrared rays irradiated from the object being measured, and the isothermal means be positioned outside a region where infrared rays irradiated pass through the infrared-ray transmitting portion to be incident upon the infrared-ray sensor.

Also, the isothermal means may comprise a mount portion, to which the object-side portion is mounted.

Also, the invention provides a radiation thermometer provided with an infrared-ray sensor for measuring a quantity of infrared rays irradiated from an object being measured, sensor-temperature measuring means for measuring a temperature of the infrared-ray sensor, and temperature calculating means for calculating a temperature of the object being measured, on the basis of a quantity of infrared rays irradiated from the object being measured, and a temperature of the infrared-ray sensor; wherein the temperature calculating means has the function of calculating a temperature of the object being measured, according to a status of the object being measured.

With such constitution, calculation of temperature is made according to a status of an object being measured, so that it is possible to suppress measurement errors to make temperature measurement of high accuracy.

Here, the status of an object being measured includes a kind of the object being measured, a portion of the object being measured, measured by the radiation thermometer, as well as the positional relationship of the object being measured, relative to the radiation thermometer.

Also, there may be provided status specifying means for specifying a status of the object being measured, and the temperature calculating means may calculate a temperature of the object being measured, according to a status specified by the status specifying means.

Also, there may be provided a probe receiving therein the infrared-ray sensor and the sensor-temperature measuring means and inserted into an opening, and a plurality of temperature sensors as the status specifying means arranged along a direction, in which the probe is inserted.

Also, there may be provided a probe receiving therein the infrared-ray sensor and the sensor-temperature measuring means and inserted into an opening, and a temperature sensor as the status specifying means provided on a base side opposed to a direction, in which the probe is inserted.

Also, the status specifying means may have the function of specifying a status of the object being measured, on the basis of information of variation of the sensor-temperature measuring means.

Also, the status specifying means may have the function of specifying a status of the object being measured, on the basis of a phase lead component of results of measurement of the sensor-temperature measuring means.

Also, the status specifying means may have the function of specifying which one of plural statuses of object being measured, the plural statuses being beforehand set.

Also, it is preferable that there be provided the device intended for at least either of adjustment of and proof of accuracy of the radiation thermometer, as the object being measured to be specified.

Here, the device intended for at least either of adjustment of and proof of accuracy of the radiation thermometer includes a device, such as a blackbody furnace or the like, used at the time of shipment of the radiation thermometer, repair thereof and the like.

Also, the status specifying means preferably has the function of specifying the object being measured, as the device intended for at least either of adjustment of and proof of accuracy of the radiation thermometer, in the case where a predetermined change in radiation temperature is detected after power is turned on.

Also, there may be provided informing means for informing realization of a predetermined condition in the case where the condition is realized when the object being measured is specified to be the device intended for at least either of adjustment of and proof of accuracy of the radiation thermometer.

Also, there may be provided display means for displaying a measured temperature with a predetermined accuracy, and the display means may have the function of displaying the measured temperature with a higher accuracy than the predetermined accuracy in the case where the object being measured is specified to be the device intended for at least either of adjustment of and proof of accuracy of the radiation thermometer.

Here, accuracy, with which a measured temperature is displayed, includes the number of places of the measured temperature.

Also, the display means preferably has the function of displaying a measured temperature in a region, in which temperature unit is displayed in the case where a measured temperature is displayed with the predetermined accuracy, with the heightened accuracy.

Also, the invention provides a radiation thermometer provided with an infrared-ray sensor for measuring a quantity of infrared rays irradiated from an object being measured, sensor-temperature measuring means for measuring a temperature of the infrared-ray sensor, a probe receiving therein the infrared-ray sensor and the sensor-temperature measuring means and inserted into an opening, and temperature calculating means for calculating a temperature of the object being measured, on the basis of a quantity of infrared rays irradiated from the object being measured, and a temperature of the infrared-ray sensor; comprising representative temperature presuming means for presuming a temperature of the infrared-ray sensor or information of a temperature representative of any one of members constituting the probe in conformity to thermal time constants peculiar to the respective members from heat conducted to the infrared-ray sensor and the members by a heat source in the vicinity of an outer wall of the probe.

Also, there may be provided temperature difference information presuming means for calculating at least either of a phase lead component and a phase lag component of results of measurement of the sensor-temperature measuring means in conformity to thermal time constants of the members present on a heat conduction path passing through the sensor-temperature measuring means to presume a temperature difference information between the sensor-temperature measuring means and at least either of the infrared-ray sensor and the members.

Also, at least either of information including a difference of results of measurement of the sensor-temperature measuring means as the phase lead component and information including a weighted mean of results of measurement of the sensor-temperature measuring means as the phase lag component may be calculated.

Also, there may be provided infrared-ray output correcting means for correcting results of measurement by the infrared-ray sensor continuously from the time of turning on the power on the basis of a temperature presumed by the representative temperature presuming means.

Also, there may be provided infrared-ray output correcting means for correcting results of measurement by the infrared-ray sensor continuously from the time of turning on the power on the basis of temperature difference information presumed by the temperature difference information presuming means.

Also, the infrared-ray output correcting means preferably has the function of correcting results of measurement by the infrared-ray sensor on the basis of changes of that temperature, which is presumed by the representative temperature presuming means, since the start of measurement of a radiation temperature of the object being measured.

Also, the infrared-ray output correcting means preferably has the function of correcting results of measurement by the infrared-ray sensor on the basis of changes of that temperature difference information, which is presumed by the temperature difference information presuming means, since the start of measurement of a radiation temperature of the object being measured.

Also, there may be provided insertion detecting means for detecting insertion of the probe into the opening, and the infrared-ray output correcting means preferably has the function of correcting results of measurement by the infrared-ray sensor on the basis of changes of that temperature, which is presumed by the representative temperature presuming means, since the time of detection of insertion by the insertion detecting means.

Also, there may be provided insertion detecting means for detecting insertion of the probe into the opening, and the infrared-ray output correcting means preferably has the function of correcting results of measurement by the infrared-ray sensor on the basis of changes of temperature difference information, which is presumed by the temperature difference information presuming means, since the time of detection of insertion by the insertion detecting means.

BRIEF DESCRIPTION OF DRAWINGS

FIG. 9(b) is a graph showing the relationship between temperature changes in a second in a thermistor and temperature differences between a tip end of a can portion of a thermopile casing and the thermistor.

BEST MODE FOR CARRYING OUT THE INVENTION

Figure 1:
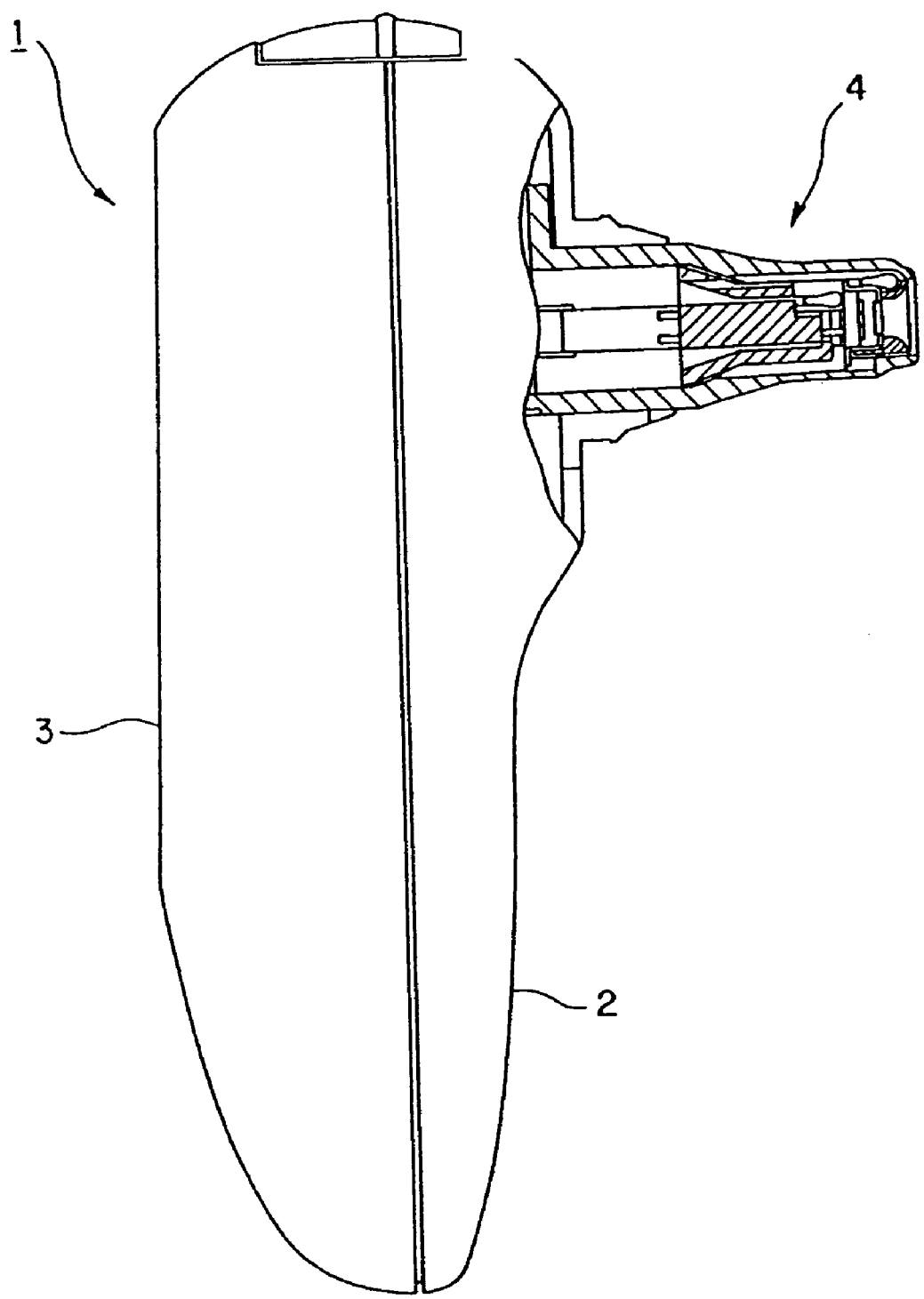
FIG. 1 is a general view showing a thermometer according to a first embodiment.

The invention will be described below based on embodiments shown in the drawings.

Figure 2:
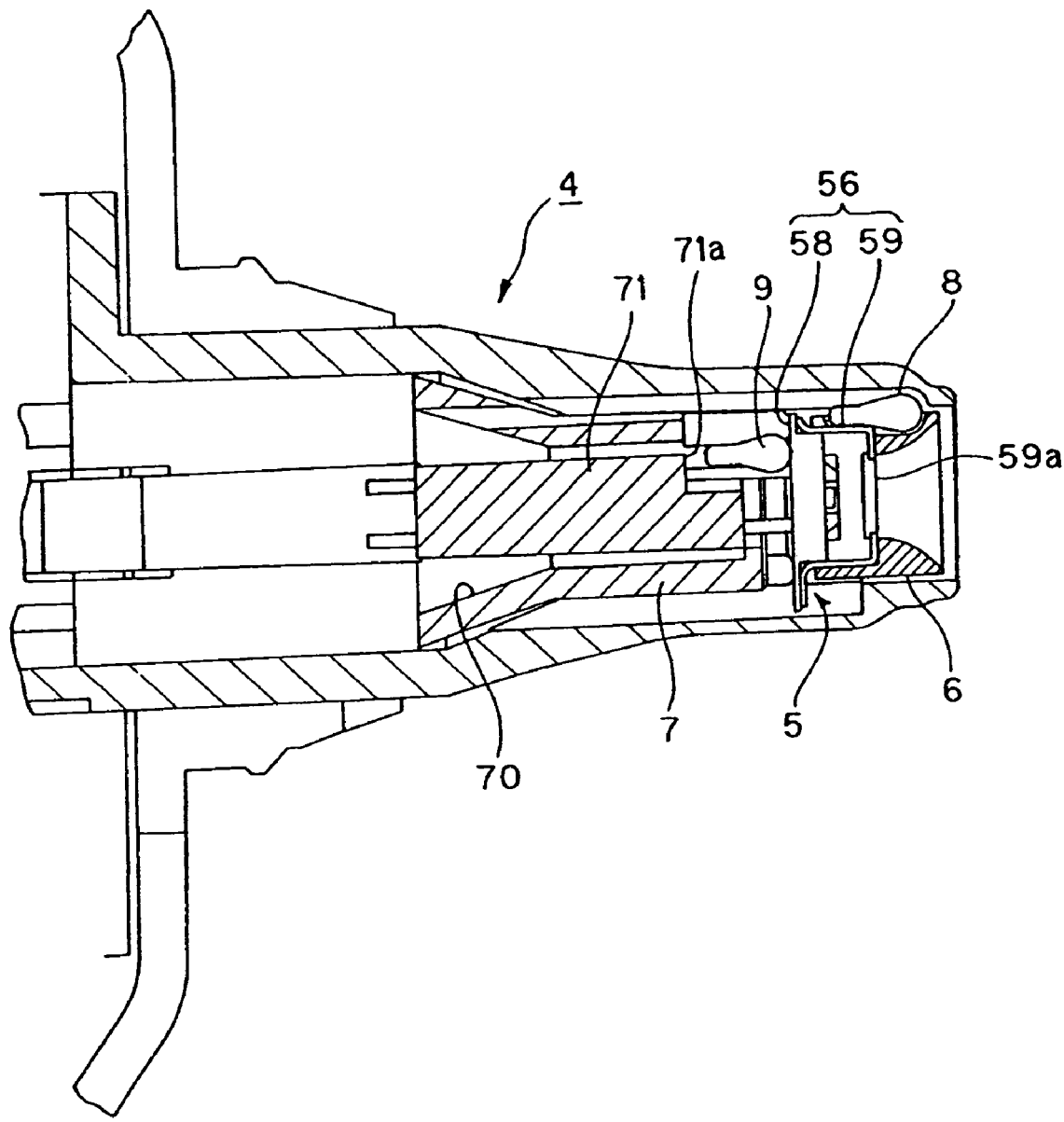
FIG. 2 is a cross sectional view showing the construction of a probe.
Figure 3:
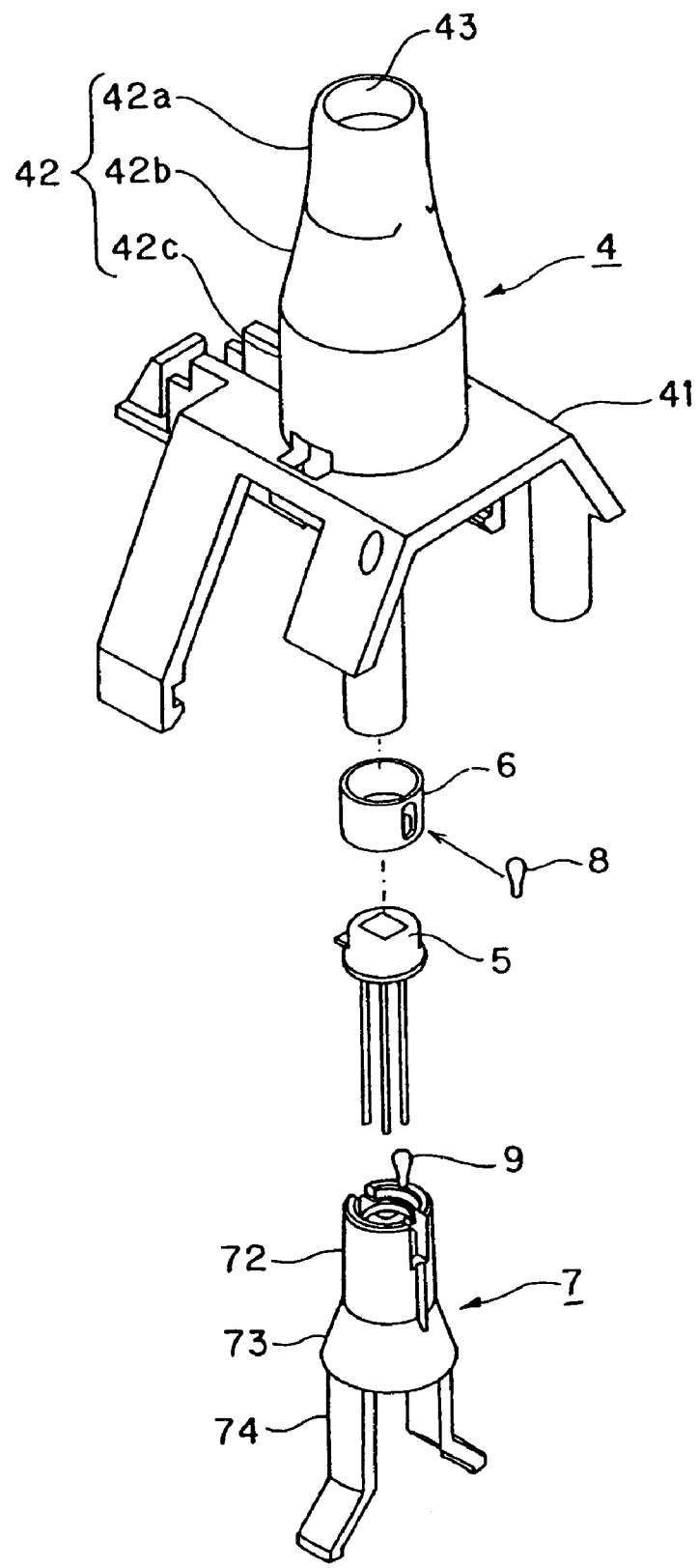
FIG. 3 is an exploded perspective view showing the internal construction of the probe.
Figure 4:
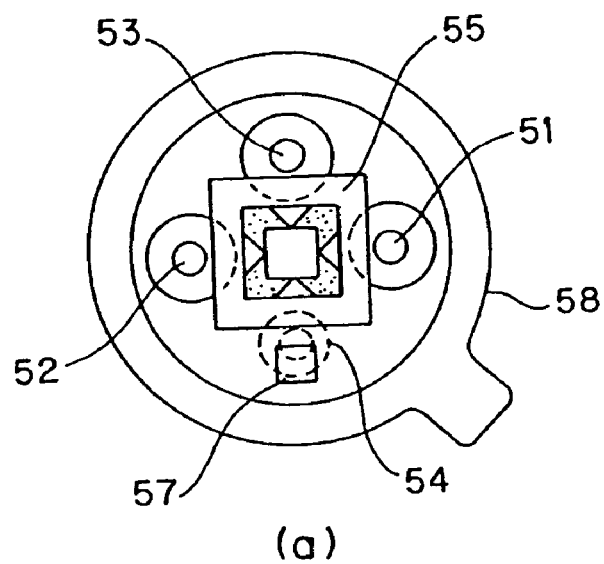
FIGS. 4(a) and 4(b), respectively, are a plan view and a cross sectional view showing the constitution of a thermopile sensor.
Figure 4:
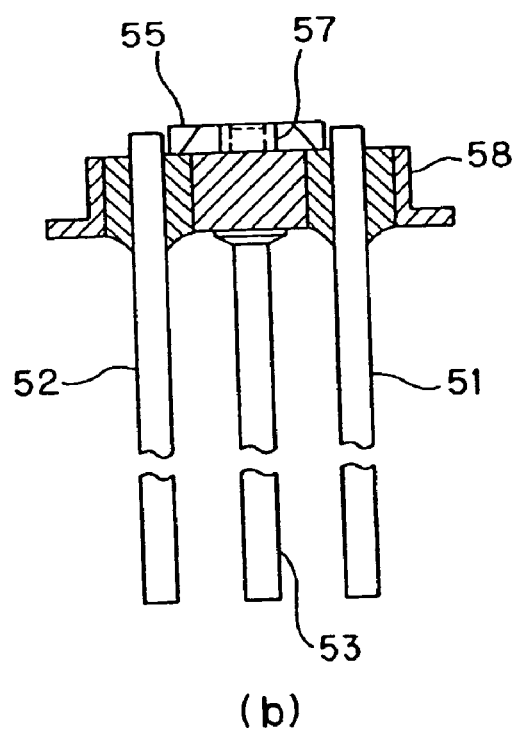
Figure 5:
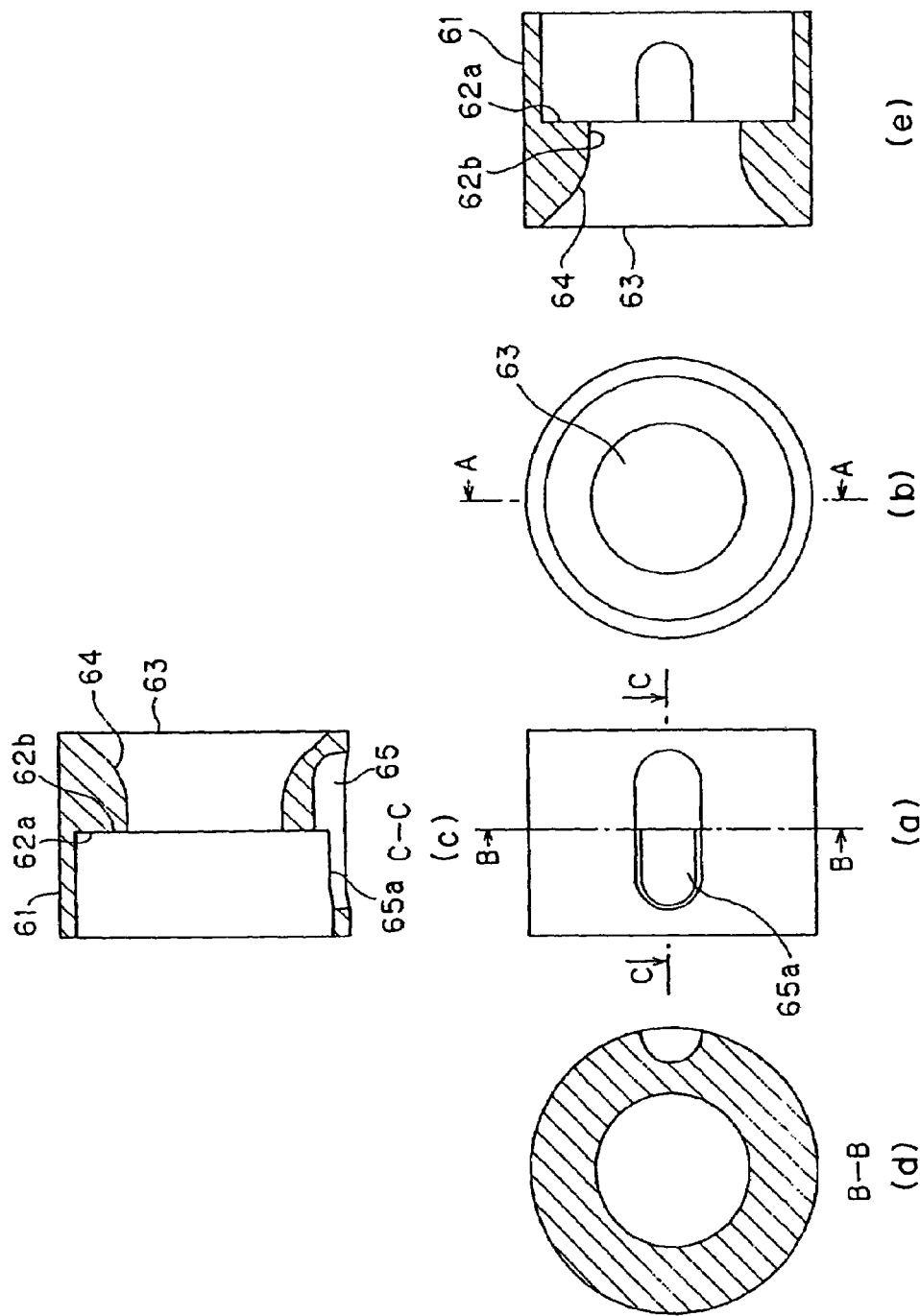
FIG. 5 is a view showing the construction of a sensor cover.

FIG. 1 is a general view showing a thermometer with a part thereof broken, according to the present embodiment. FIG. 2 is a cross sectional view showing an internal construction of a probe. FIG. 3 is an exploded perspective view showing the internal construction of the probe. FIGS. 4(a) and 4(b) are a plan view and a cross sectional view showing the constitution of a thermopile sensor (a can portion is omitted in the figures). FIG. 5 is a view showing the construction of a sensor cover.

As shown in FIG. 1, the thermometer 1 is mainly composed of a main body 3 having a grip portion 2 being gripped by a user, and a columnar-shaped probe 4 projecting in a direction substantially perpendicular to the body 3.

Provided in the probe 4 are a thermopile sensor 5, a sensor cover 6, a holder 7, a first thermistor 8, and a second thermistor 9.

The probe 4 is substantially cylindrical-shaped to mainly comprise a mount portion 41 fitted into the body 3, and a cylindrical portion 42 formed projectingly on the mount portion 41. The cylindrical portion 42 comprises a small-diameter tip end 42a, a diverging slant surface portion 42b, and a large-diameter base 42c. Received in the cylindrical portion 42 are the sensor cover (isothermal means) 6, the thermopile sensor 5, the holder 7, the first thermistor (sensor-temperature measuring means, temperature distribution measuring means) 8, and the second thermistor (sensor-temperature measuring means) 9.

The thermopile sensor 5 is in the form of a flattened column, and lead wires 51 to 54 are taken out from an end surface thereof. The thermopile sensor 5 is mainly composed of a thermopile chip (infrared-ray sensor) 55, a thermopile casing (infrared-ray sensor receiving member) 56, and an integrated thermistor (sensor-temperature measuring means) 57. The thermopile casing 56 is composed of a substantially disk-shaped stem portion 58, to which the thermopile chip 55 is mounted, and a bottomed cylinder-shaped can portion (side of an object being measured) 59 covering front and side of the thermopile chip 55. Supported centrally on a top of the stem portion 58 is the substantially square thermopile chip 55, and arranged adjacent to one side of the thermopile chip is the integrated thermistor 57. An end of the lead wire 53 for taking out an output of the integrated thermistor 57 is exposed to the top of the stem portion 58 to be disposed adjacent a side opposed to the integrated thermistor 57 with the thermopile chip 55 interposed therebetween, and ends of the lead wires 51, 52 for taking out an output of the thermopile chip 55 are exposed to the top of the stem portion to be disposed adjacent the other two sides. The lead wires 51 to 54, respectively, are taken out from an underside of the stem portion 58 through an interior thereof. Also, the ground wire 54 common to the integrated thermistor 57 and the thermopile chip 55 is taken out from an underside of the stem portion 58 below a position where the integrated thermistor 57 is mounted. The can portion 59 of the thermopile casing 56 has a window (infrared-ray transmitting portion) 59a made of silicon glass in a position opposed to the thermopile chip 55. An edge of the can portion 59 on a opening side thereof and a peripheral edge of the stem portion 58 are joined together to thereby seal an interior of the thermopile casing 56.

The holder 7 is composed of a cylindrical portion 72 in the form of a substantially cylinder with a partition 71 provided in a hole 70 to support the thermopile sensor 5, a diverging slant surface portion 73 adjacent to the cylindrical portion, and a leg portion 74 being mounted on the body 3. The cylindrical portion 72 and the slant surface portion 73 of the holder 7, respectively, are fitted into and mounted to interiors of the tip end 42a and surface portion 42b of the probe 4. The thermopile sensor 5 is mounted on an end of the cylindrical portion 72. At this time, the lead wires 51 to 54 taken out from the thermopile sensor 5 are separated from one another by the partition 71. Also, the partition 71 is partially formed with a notch 71a, which receives the second thermistor 9. The second thermistor 9 received in the notch 71a is disposed between the lead wires to measure a temperature of the stem portion 58 of the thermopile casing 56.

The sensor cover 6 assumes a substantially cylindrical shape. FIGS. 5(a), 5(b), 5(c), 5(d), and 5(e), respectively, are a front view, right-side view, C—C cross sectional view, B—B cross sectional view, and a A—A cross sectional view. Formed in the sensor cover 6 is a large-diameter portion (mount portion) 61 having a constant inner diameter in an axial direction toward the thermopile sensor and extending up to a substantially center in the axial direction. Formed adjacent to the large-diameter portion 61 is a step 62 having a radial end surface 62a, and formed contiguous to the step 62 is a diverging portion 64, of which an inner periphery diverges toward an opening 63. Also, formed on a part of an outer periphery is a first thermistor receiving portion 65, which is lengthy in the axial direction. Formed on a large-diameter portion side of the first thermistor receiving portion 65 is an opening 65a communicated to an interior of the cover. The sensor cover 6 is disposed on an inner peripheral side of the tip end 42a of the probe 42 in such a manner that a large-diameter portion side of the sensor cover 6 is put in contact with the opening of the probe. An outer peripheral surface of the thermopile sensor 5 is fitted into the inner peripheral surface of the large-diameter portion of the sensor cover 6. At this time, a window-side end surface of the can portion 59 of the thermopile sensor cover 6 abuts against the end surface 62a of the step 62b of the sensor cover 6, so that a step-side inner peripheral edge of the diverging portion 64 of the thermopile sensor cover 6 surrounds a periphery of the window 59a and exposes the window 59a toward an opening 43 of the probe 4.

Here, the first thermistor 8 and the second thermistor 9 are arranged in substantially the same position in a circumferential direction about an axis of the probe 4. Also, the integrated thermistor 57 is arranged in a position in which the thermopile chip 55 is interposed between the integrated thermistor 57, and the first thermistor 8 and the second thermistor 9.

Figure 6:
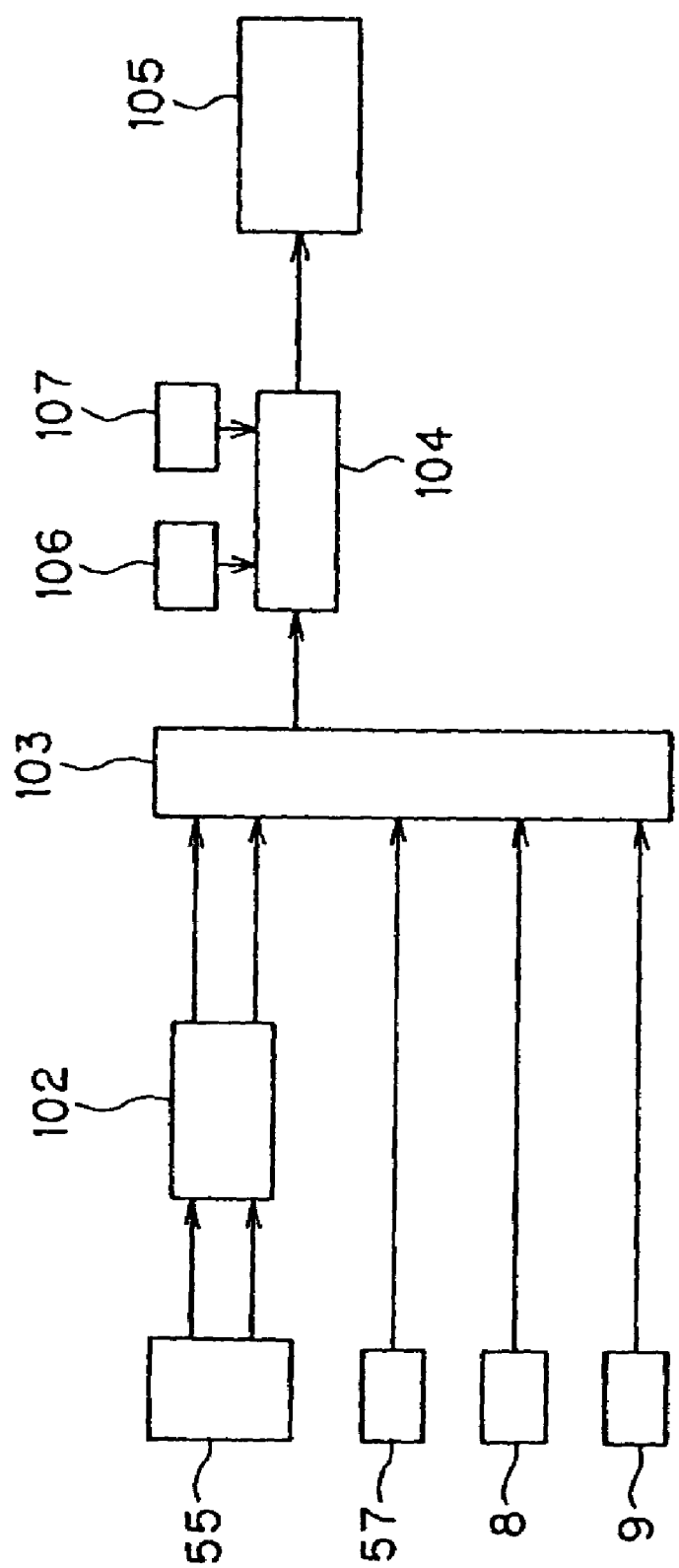
FIG. 6 is a block diagram showing an internal constitution of the thermometer.

FIG. 6 is a block diagram showing an outline of an internal constitution of a thermometer.

The thermometer is mainly composed of the thermopile chip 55 for detecting infrared rays irradiated from an eardrum, an amplifier 102 for amplifying an output signal from the thermopile chip 55, the integrated thermistor 57 for detecting a temperature of the thermopile chip 55, the first thermistor 8 disposed in front of the thermopile sensor 5, the second thermistor 9 disposed behind the thermopile sensor 5, an A/D converter 103 for converting analog signals outputted from the amplifier 102, the integrated thermistor 57, the first thermistor 8, and the second thermistor 9 into a digital signal, a CPU (temperature calculating means) 104 for making predetermined calculation and judgment processings on a digital signal outputted from the A/D converter 103 to calculate a body temperature or the like, a display unit (LCD) 105 for displaying information, such as measurements of body temperature or the like, obtained in the calculation and judgment processings in the CPU 104, a power switch 106 for breaking and making supply of power to the whole equipment, and a measurement start switch 107 for commanding the start of body temperature measurement.

Figure 7:
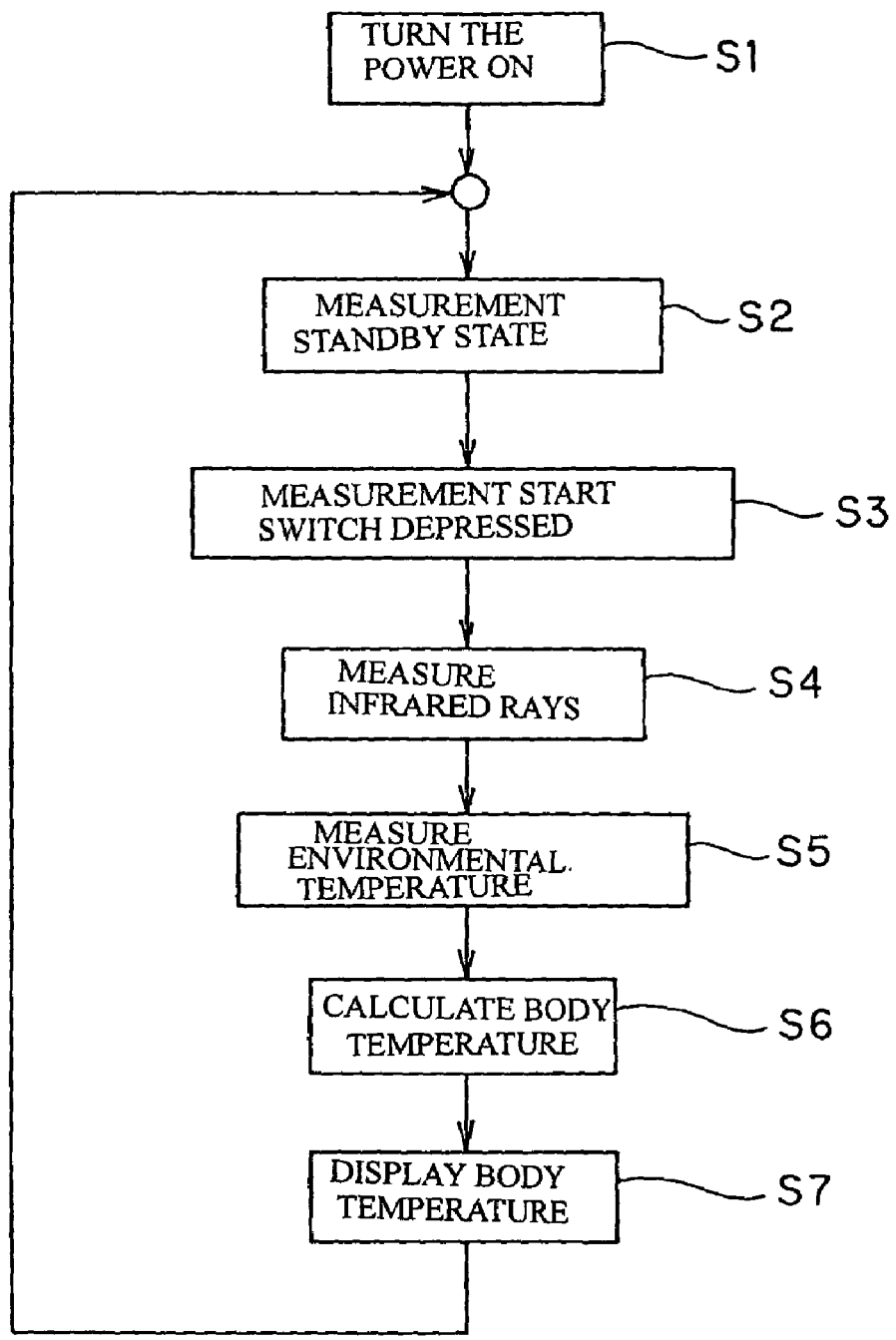
FIG. 7 is a flowchart showing the procedure of measurement of body temperature with the use of the thermometer.

Subsequently, the procedure of body temperature measurement by means of the thermometer 1 will be described with reference to FIG. 7.

First, when the power switch 106 is made ON (STEP 1), the thermometer is put in a measurement standby state (STEP 2). In this state, when the measurement start switch 105 is depressed (STEP 3), the thermopile sensor 5 is used to measure an amount of infrared rays (STEP 4) and the thermistor 57 is used to measure an environmental temperature (STEP 5). Based on the amount of infrared rays and the environmental temperature, a body temperature is calculated in the CPU 104 (STEP 6). The calculated body temperature is displayed on the display unit 105 (STEP 7), and the procedure is returned to STEP 2.

Here, an explanation will be given to the method of calculating a body temperature in STEP 6.

Where E indicates an output of the thermopile sensor 5, $T_x$ indicates temperature of an object, $T_a$, $T_1$, $T_2$, respectively, indicate temperatures of the integrated thermistor 57, the first thermistor 8, and the second thermistor 9, L1, L2, a, b are constants, and $T_d=(aT_a+bT_2)/(a+b)$ is assumed, the following expression of relations $$E=L1(T_x^4-T_d^4)+L2(T_1^4-T_d^4)$$

is derived from the above, so that it is possible to calculate temperature of an object based on $$T_x=[\{E-L2(T_1^4-T_d^4)/L1+T_d^4\}]^{1/4}.$$

That is, with the thermometer 1, the integrated thermistor 57 and the first thermistor 8 are arranged in a position, in which the thermopile chip 55 is interposed therebetween, and so a temperature $T_d$ of a cold junction of the thermopile chip 55 disposed in an intermediate position therebetween can be predicted from a temperature $T_a$ of the integrated thermistor 57 and a temperature $T_1$ of the first thermistor 8. With such status, the cold junction temperature of the thermopile chip 55 can be calculated further precisely as compared with the case where the cold junction temperature of the thermopile chip 55 is calculated by means of only the integrated thermistor 57. Accordingly, a temperature of an object, that is, a body temperature can be measured precisely. Also, a shape of the sensor cover 6, which is gradually reduced in diameter from the opening 63 to the window 59a, makes it possible to suppress incidence of infrared rays through the window 59a from other things than an object, but it is not possible to eliminate influences of infrared rays irradiated from the can portion 59 of the thermopile casing 56 disposed in front of a hot junction of the thermopile chip 55. With the thermometer 1, however, the first thermistor 8 is used to enable measuring a temperature of the can portion 59 of the thermopile casing 56, so that it is possible to correctly evaluate influences of infrared rays from the can portion 59 of the thermopile casing 56. Accordingly, it is possible to calculate a temperature of an object further correctly. Also, by providing the sensor cover 6 closely on a front surface portion of the thermopile casing 56 and forming the cover from a material, such as gold, silver, copper, aluminum or the like, having a good thermal conductivity, it is possible to suppress generation of the temperature distribution on a front surface portion of thermopile casing 6. Accordingly, by using the first thermistor 8 to measure a temperature of one point on the front surface portion of thermopile casing 6, it is possible to precisely measure a temperature of the front surface portion of the thermopile casing 56. Also, even when a temperature of the sensor cover 6 is measured by the first thermistor 8 to thereby approximate a temperature of the thermopile casing 56, an amount of infrared rays irradiated from the can portion 59 on the front surface portion of the thermopile casing 56 can be precisely estimated. Further, since the sensor cover 6 is shaped to be outside a field of view of the thermopile chip 55 through the window 59a, irradiation of infrared rays from the sensor cover 6 can be prevented from having influences on measurement of temperature of an object. Also, this eliminates the need of performing any specific surface processing, such as gold-plating or the like, on the sensor cover.

(Second Embodiment)

An explanation will be given below to a second embodiment of the invention.

Figure 8:
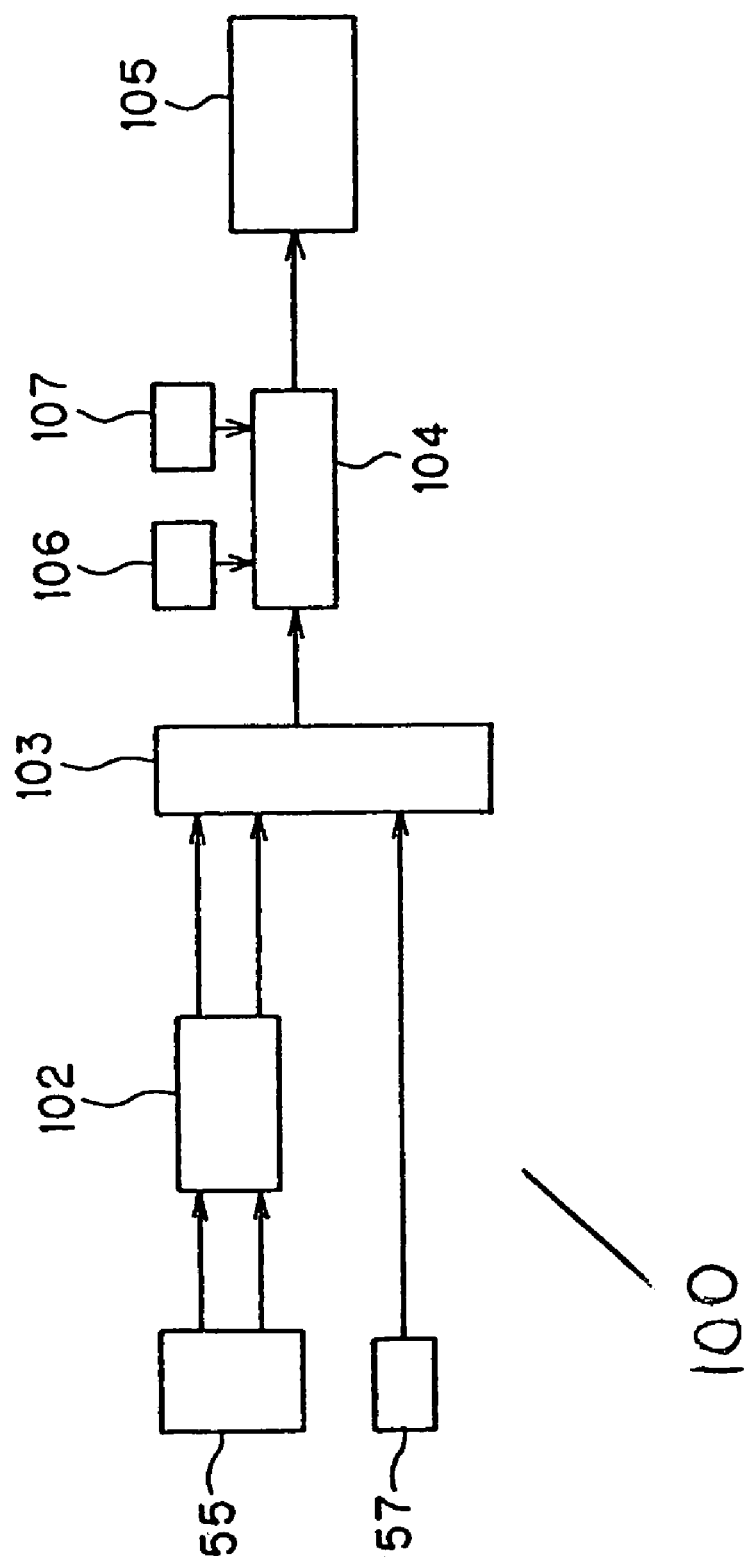
FIG. 8 is a block diagram showing an outline of an internal construction of an ear type thermometer according to a second embodiment.

FIG. 8 shows an outline of an internal construction of an ear type thermometer 100 according to a second embodiment of the invention.

Since the ear type thermometer 100 is constructed in the same manner as the thermometer 1 according to the first embodiment except that there are not provided the first thermistor and the second thermistor and that a formula for a temperature of an object is correspondingly different from that in the first embodiment, the same reference characters denote the same constituents and an explanation therefor will be omitted.

First, the measurement principle for the thermometer 100 will be described.

Figure 9:
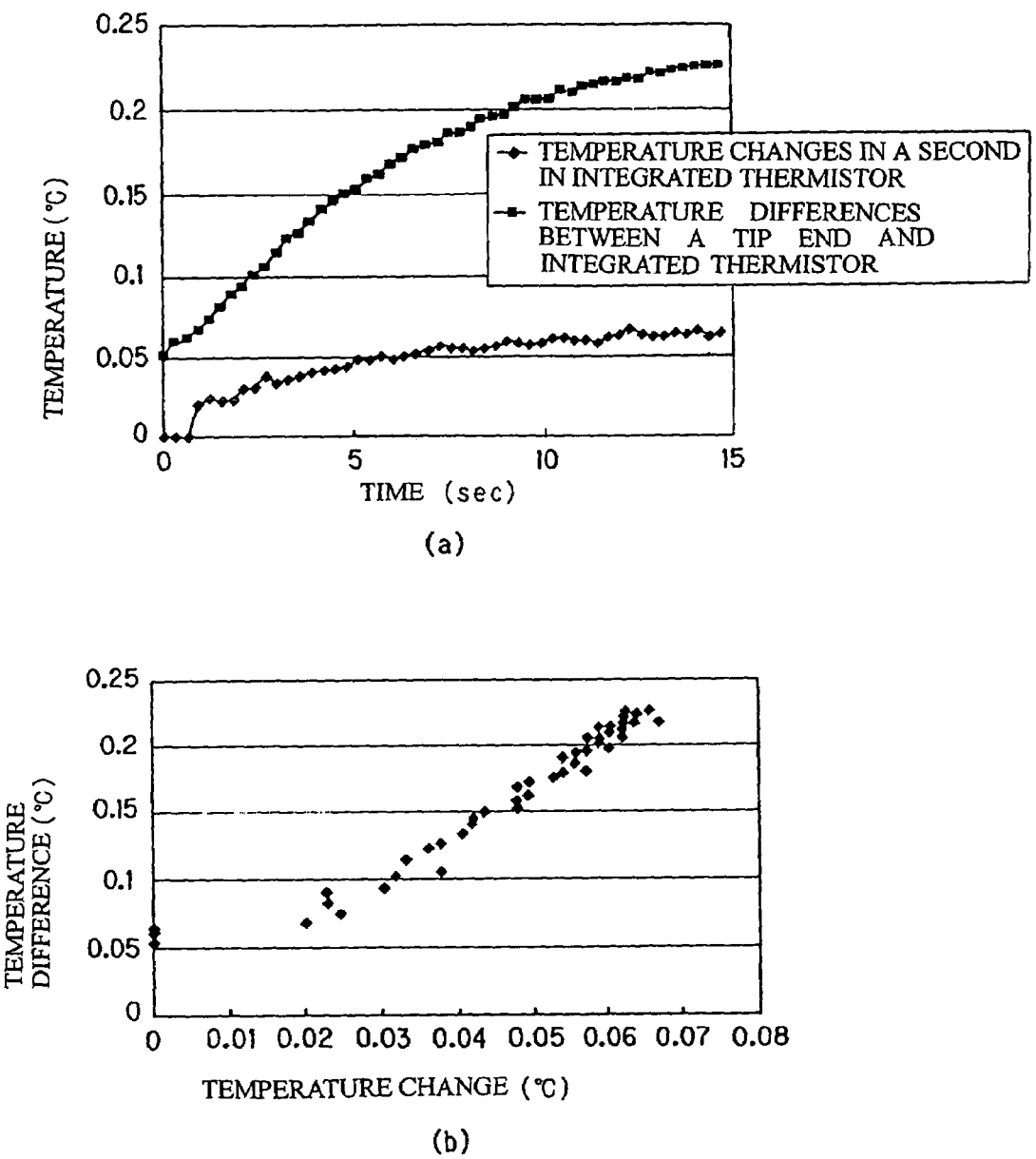
FIG. 9 is a graph showing sampling of temperature changes in a second in an integrated thermistor and temperature differences between a tip end of a can portion of a thermopile casing and the thermistor.
Figure 10:
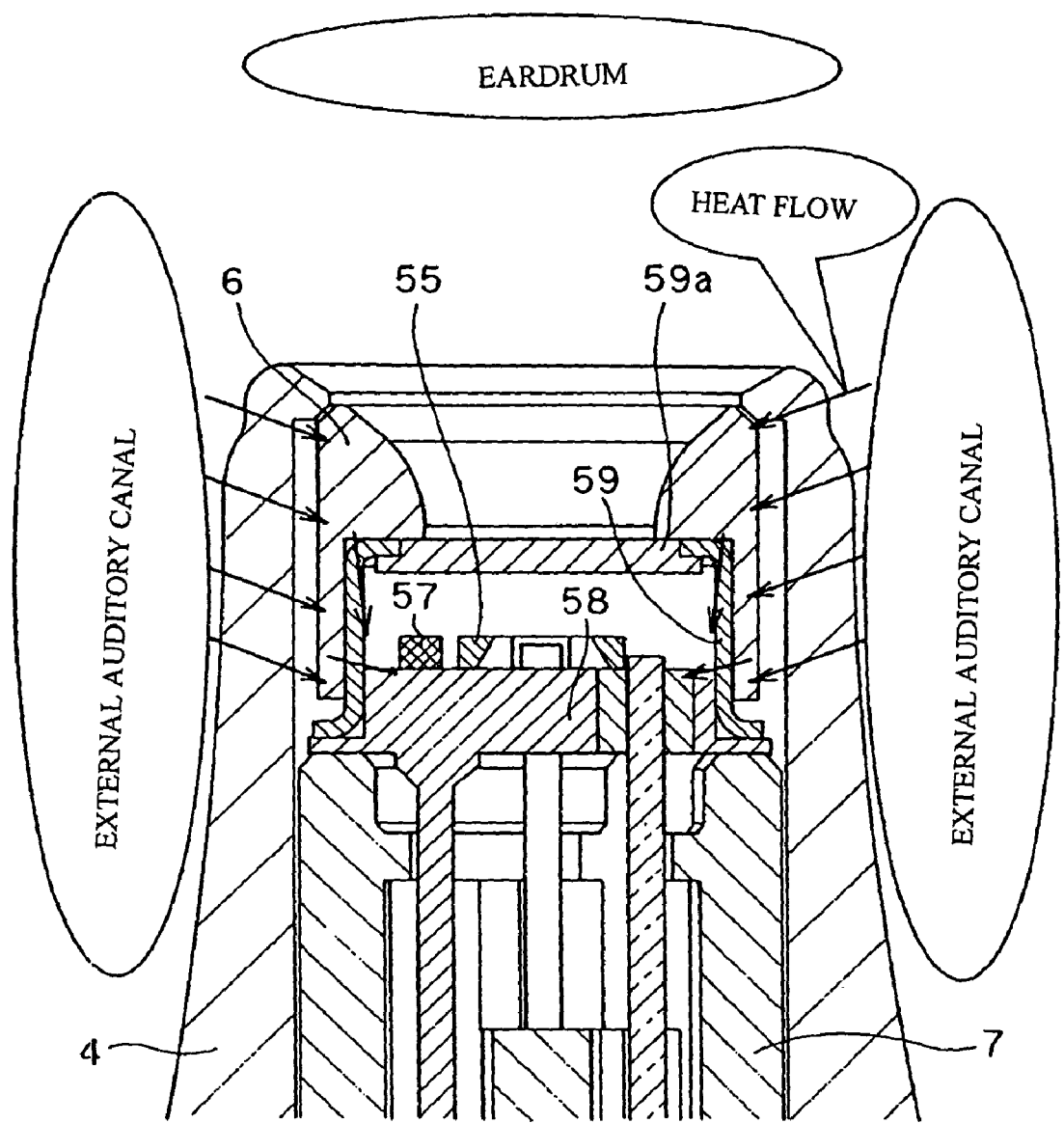
FIG. 10 is a view illustrating a heat flow around a thermopile sensor.

FIG. 9(a) is a graph showing sampling of temperature changes in a second in an integrated thermistor 57 housed in a thermopile sensor and temperature differences between a tip end of a can portion 59 of a thermopile casing 56 and the integrated thermistor 57 where the abscissa represents time and the ordinate represents temperature. FIG. 9(b) is a graph showing a plot of data shown in FIG. 9(a) where the abscissa represents temperature changes in a second in the integrated thermistor 57 and the ordinate represents temperature differences between a front surface portion of the can portion 59 of the thermopile casing 56 and the integrated thermistor 57.

As shown in FIG. 9(a), when comparison is made between temperature changes ($T_a(t)-T_a(t-1)$ t: time) at each time in the integrated thermistor 57 and temperature differences between the front surface portion of the can portion 59 and the integrated thermistor 57, substantially the same changes are shown and it is found from FIG. 9(b) that the both are closely correlated with each other.

This is because heat of an external auditory canal contacting with an outer peripheral surface of a probe 4 is conducted to the probe 4→a thermopile cover 6→the can portion→a stem portion 58→the integrated thermistor 57/a thermopile chip 55 whereby correlation is generated between temperature differences between the front surface portion of the can portion 59 and the integrated thermistor 57 present in the heat flow path and temperature changes in a second in the integrated thermistor 57, caused by the conducted heat.

Accordingly, it is possible from temperature changes in the integrated thermistor 57 to estimate temperature differences between the front surface portion of the can portion 59 and the integrated thermistor 57, and to calculate an amount of infrared rays irradiated from the front surface portion of the can portion 59.

According to the principle, assuming that $T_a$ and $T_{at}$, respectively, indicate a present temperature of the integrated thermistor 57 and a temperature of t seconds before and L3 indicates a constant, the following expression of relations $$E=L1(T_x^4-T_a^4)+L3(T_a-T_{at})$$

is derived, so that a temperature $T_x$ of an object can be calculated from $$T_x=[\{E-L3(T_1-T_d)/L1+T_d^4\}]^{1/4}$$

By doing this, with only the integrated thermistor 57 housed in the thermopile sensor 5, it is possible to precisely estimate an amount of infrared rays irradiated from the front surface portion of the can portion 59 of the thermopile casing 56 to precisely calculate a temperature of an object.

(Third Embodiment)

An explanation will be given below to a third embodiment of the invention.

An internal constitution of an ear type thermometer according to the embodiment is the same as that of the thermometer 100 shown in FIG. 8. The same constituents as those in the first and second embodiments are denoted by the same reference characters, and an explanation therefor will be omitted. In the present embodiment, a feature amount of an object being measured is detected by an integrated thermistor 57 housed in a thermopile sensor 5.

Figure 11:
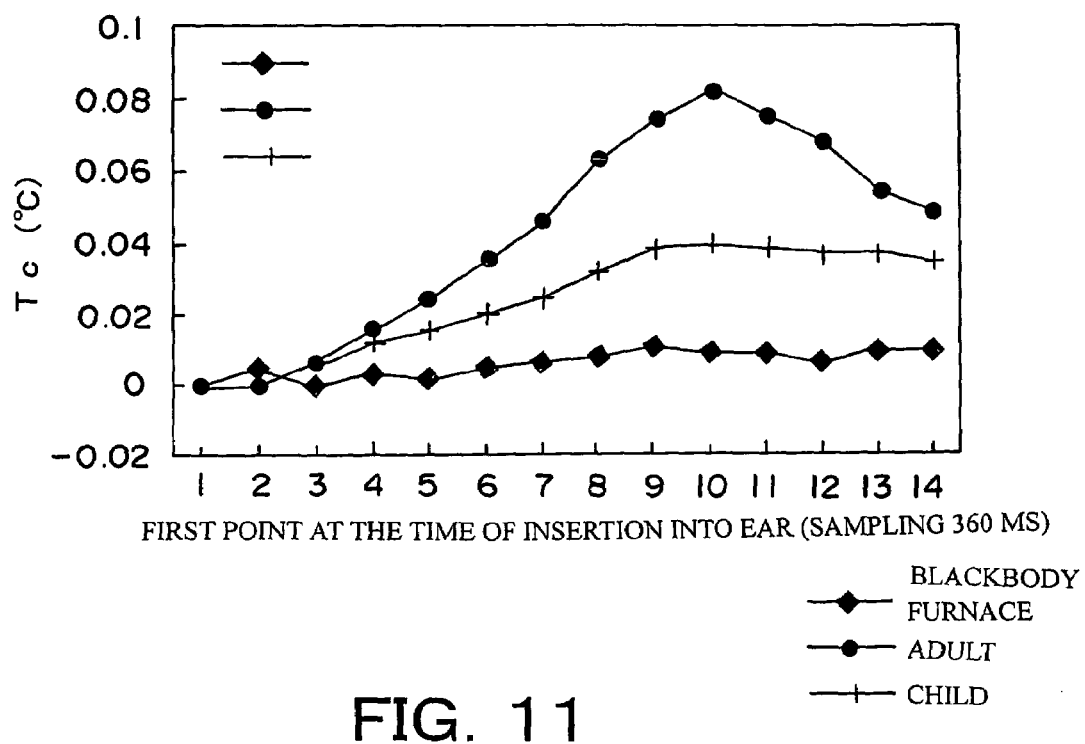
FIG. 11 is a graph showing changes of $T_c$ immediately after a probe is inserted.

Assuming that $T_a$ indicates an output of the integrated thermistor 57, $T_b$ indicates a difference information of $T_a$, and $T_c$ indicates a difference information of $T_b$, a maximum value of $T_c$ is varied depending upon whether an object being measured, as shown in FIG. 11, is an adult, a child, or a blackbody furnace. Here, FIG. 11 shows the behavior of $T_c$ immediately after a probe 4 is inserted into an ear, where the abscissa represents the number of times of sampling made in an interval of 360 ms and the ordinate represents $T_c$. These differences are due to the fact that a point, at which heat is input into the probe, differs depending upon an object being measured. That is, when a person being measured is an adult, an earhole is large to permit the probe 4 to be inserted deep thereinto, and so an amount of heat conducted to the probe from an outer ear is large, while when a person being measured is a child, an earhole is small to permit the probe to be inserted only shallowly thereinto, and so an amount of heat conducted to the probe from an outer ear is small. Also, in the case where a blackbody furnace is measured as described later, the probe does not contact with a radiant surface of the blackbody furnace. Accordingly, an object being measured can be featured, that is, discriminated by such information $T_c$.

Figure 12:
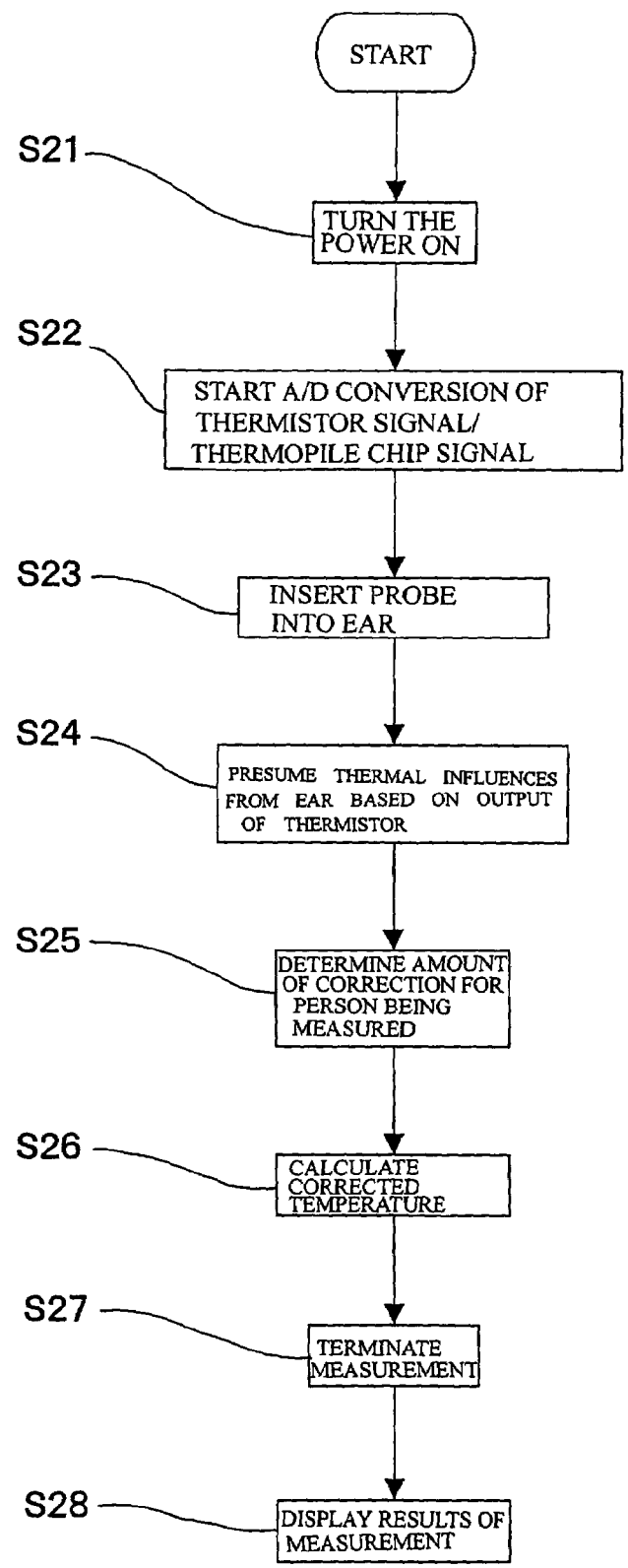
FIG. 12 is a flowchart showing the procedure of measurement of body temperature in an ear type thermometer according to a third embodiment.

FIG. 12 shows the procedure of measurement of body temperature performed by a thermometer 110 according to the embodiment.

First, when power is turned on (STEP 21), A/D conversion of a signal from the integrated thermistor 57 and a signal from the thermopile sensor 5 is started (STEP 22). Subsequently, the probe 4 is inserted into an ear (STEP 23). The CPU 104 detects the behavior of the above $T_c$ from an output of the thermistor 57 whereby thermal influences from an ear and an object being measured are presumed (STEP 24) to determine an amount of thermal correction corresponding to the object being measured (STEP 25). A corrected temperature is calculated on the basis of the determined amount of thermal correction (STEP 26), measurement is terminated (STEP 27), and results of measurement are displayed on a display unit 105 (STEP 28).

Here, an explanation will be given to a method of determining an amount of thermal correction corresponding to an object being measured and calculation of a corrected temperature on the basis of the amount of thermal correction.

Figure 13:
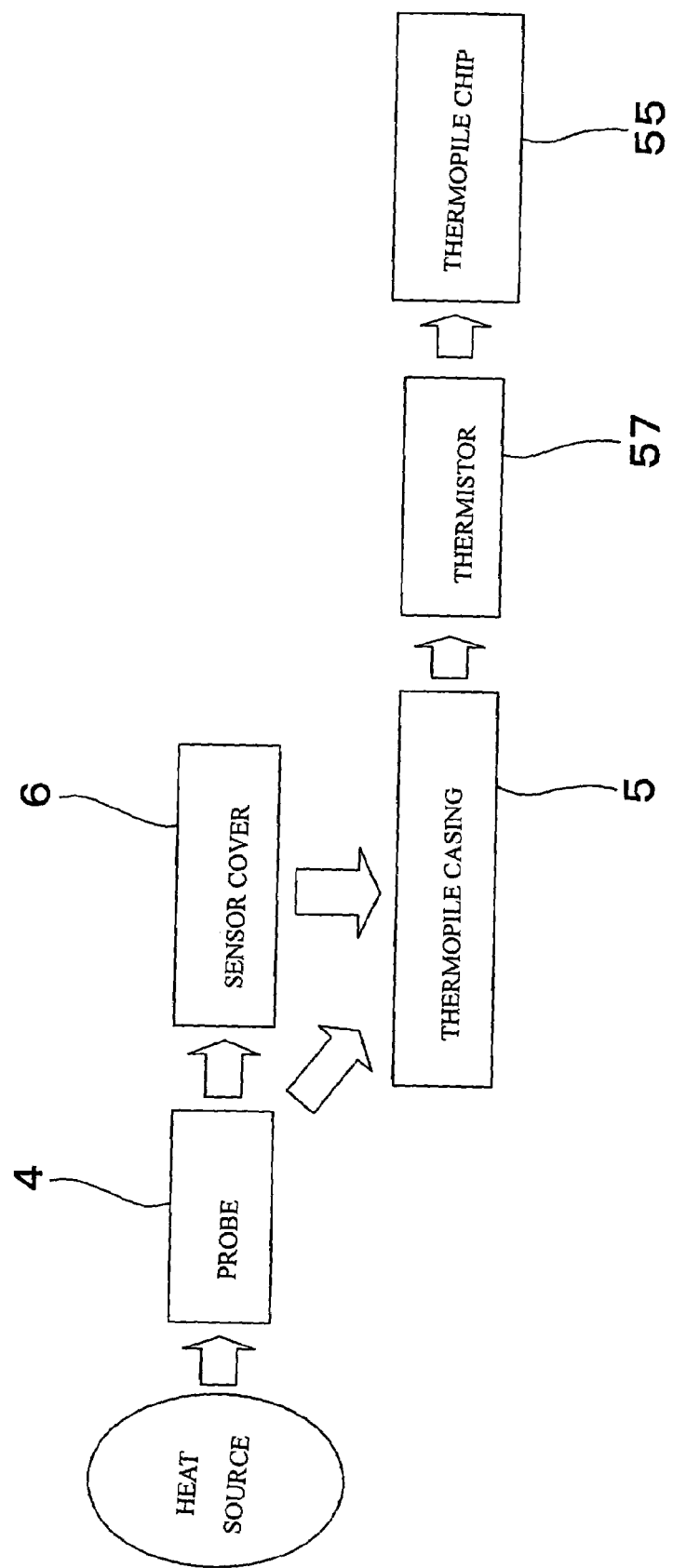
FIG. 13 is a view schematically showing a heat flow in the thermometer.

FIG. 13 schematically shows a heat flow in the thermometer 110.

First, heat flows to the probe 4 from a heat source such as an external auditory canal or the like due to radiation or conduction. Subsequently, heat is conducted to a sensor cover 6 and the thermopile casing 56 from the probe 4. Heat conducted to the thermopile casing 56 flows to a thermopile chip 55 via the integrated thermistor 57.

Figure 14:
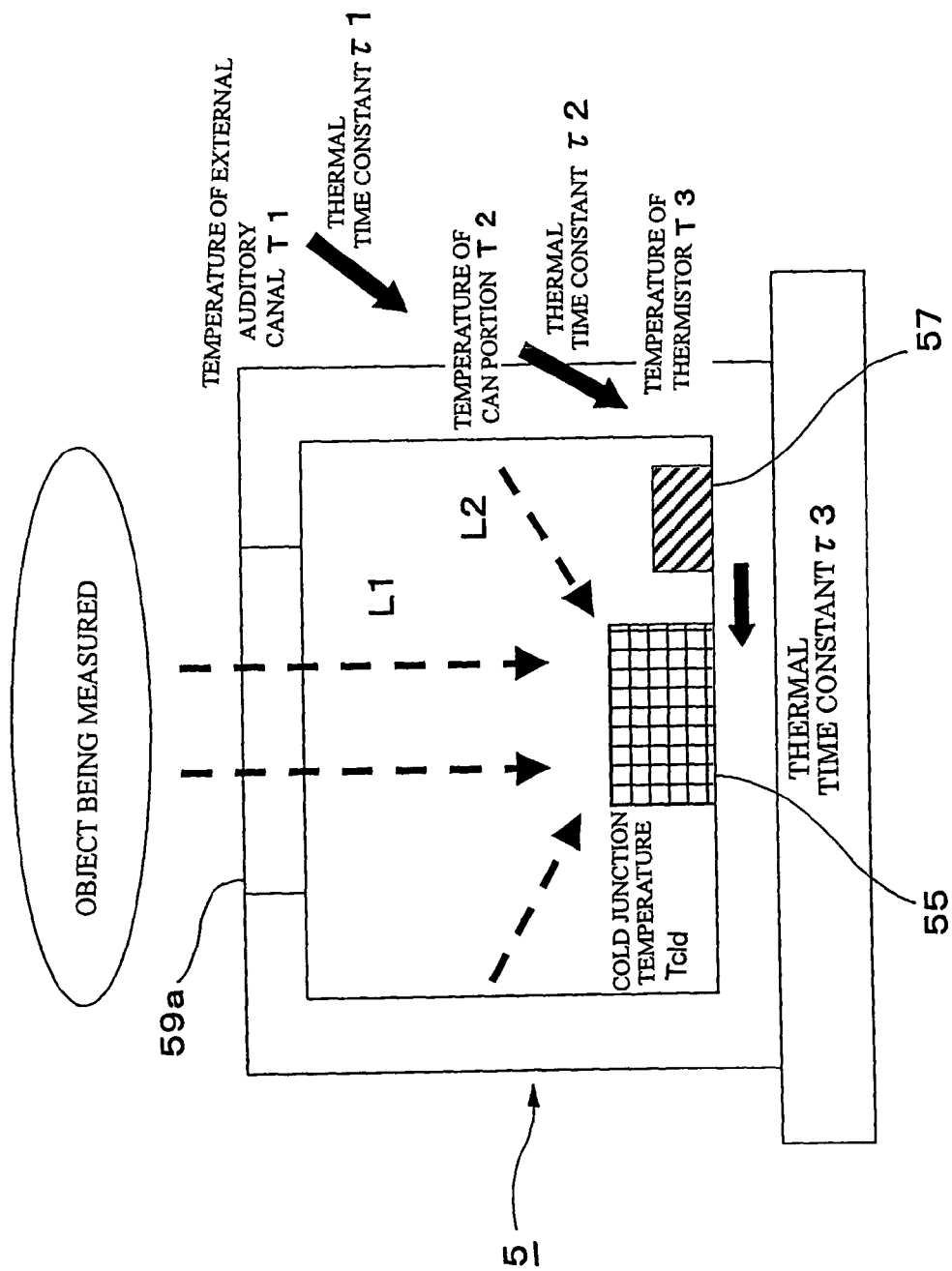
FIG. 14 is a view schematically showing a conduction path of heat around a thermopile casing.

Since thermal time constants of respective members constituting the probe 4 are determined for such heat flow from an outside heat source, representative temperatures of other members can be calculated provided that a temperature of one constituent member on a heat conduction path is found. FIG. 14 schematically shows such state around the thermopile casing 56. Here, T1 indicates a temperature of an external auditory canal, T2 a temperature of the can portion 59, T3 a temperature of the integrated thermistor 57, $T_{cld}$ a cold junction temperature of the thermopile chip 55, τ1 a thermal time constant of a member extending to the can portion 59 from an external auditory canal, τ2 a thermal time constant of a member extending to the integrated thermistor 57 from the can portion 59, and τ3 a thermal time constant of a member extending to the thermopile chip 55 from the integrated thermistor 57. Here, assuming that a temperature T3 of the integrated thermistor 57 is known, T1 and T2 make phase lead components relative to T3 in accordance with the above heat flow, and $T_{cld}$ makes a phase lag component relative to T3.

Accordingly, where T3(n) indicates respective sampling temperatures of the integrated thermistor 57, a difference information is used to enable calculating T1 as a component proportional to a temperature difference information between it and T3.

$$\alpha(T1-T3)=T3(n)-T3(n-2)$$

Meanwhile, when a thermal time constant does not match with a difference information, T2 puts off the difference information by way of weighted mean in the following manner $$\beta(T2-T3)=\{A \cdot X(n)+B \cdot X(n-1)\}/(A+B)$$

where $\alpha(T1-T3)=X$ is assumed.

Also, $T_{cld}$ can be calculated as a component proportional to a temperature difference information with respect to T3 by way of weighted mean in the following manner $$\gamma(T3-T_{cld})=\{A \cdot T3(n)+B \cdot T3(n-1)\}/(A+B)$$

Here, when constituent members of the probe 4 are present on a side (heat source side) of the probe 4 relative to the integrated thermistor 57, a phase lead information is presumed, and when the constituent members are present on a side of the thermopile chip 55, a phase lag information is used to presume a cold junction temperature of the thermopile chip 55. Thus by measuring a temperature of the integrated thermistor 57, it is possible to calculate a cold junction temperature $T_{cld}$ of the thermopile chip 55.

Where L1 indicates a sensitivity for infrared rays irradiated from an object being measured and L2 indicates a sensitivity for infrared rays irradiated from the can portion 59, an output voltage E of the thermopile chip 55 is represented by $$E=L1(T_x^4-T_{cld}^4)+L2((T2)^4-T_{cld}^4)$$

As described above, since representative temperatures of T2 and $T_{cld}$ are presumed by a temperature of the integrated thermistor 57, a temperature $T_x$ of an object being measured can be calculated from the output voltage E of the thermopile chip 55 by beforehand calibrating L1 and L2 as proper adjustment data.

Also, in the case where $T_x$ is calculated in the above manner, however, it is difficult to correctly measure T2, or calculate a biquadratic root, so that estimation can be made by development into components proportional to a temperature difference information between respective temperatures and T3 as in $$L2((T2)^4-T_{cld}^4)=\alpha(T1-T3)+\beta(T2-T3)+\gamma(T3-T_{cld})+\ldots$$

Here, for example, (T1–T3) represents a manner of heat transmission, which is different from the case where a blackbody furnace and a human body are measured. Accordingly, it suffices to set this thermal correction coefficient α at values, which are different at the time of measurement of a blackbody furnace and a human body. Also, since when a way to insert the probe into an ear is different, a manner of heat transmission is varied even in the case where the same human body is measured, an optimum value of α varies with individual persons. Therefore, by modifying the thermal correction coefficient α on the basis of influences (in other words, an object being measured) of heat, which are presumed from individual feature amounts, an amount of correction can be optimized for individual persons, thus an optimum thermal correction can be made on measurements of body temperature.

Figure 15:
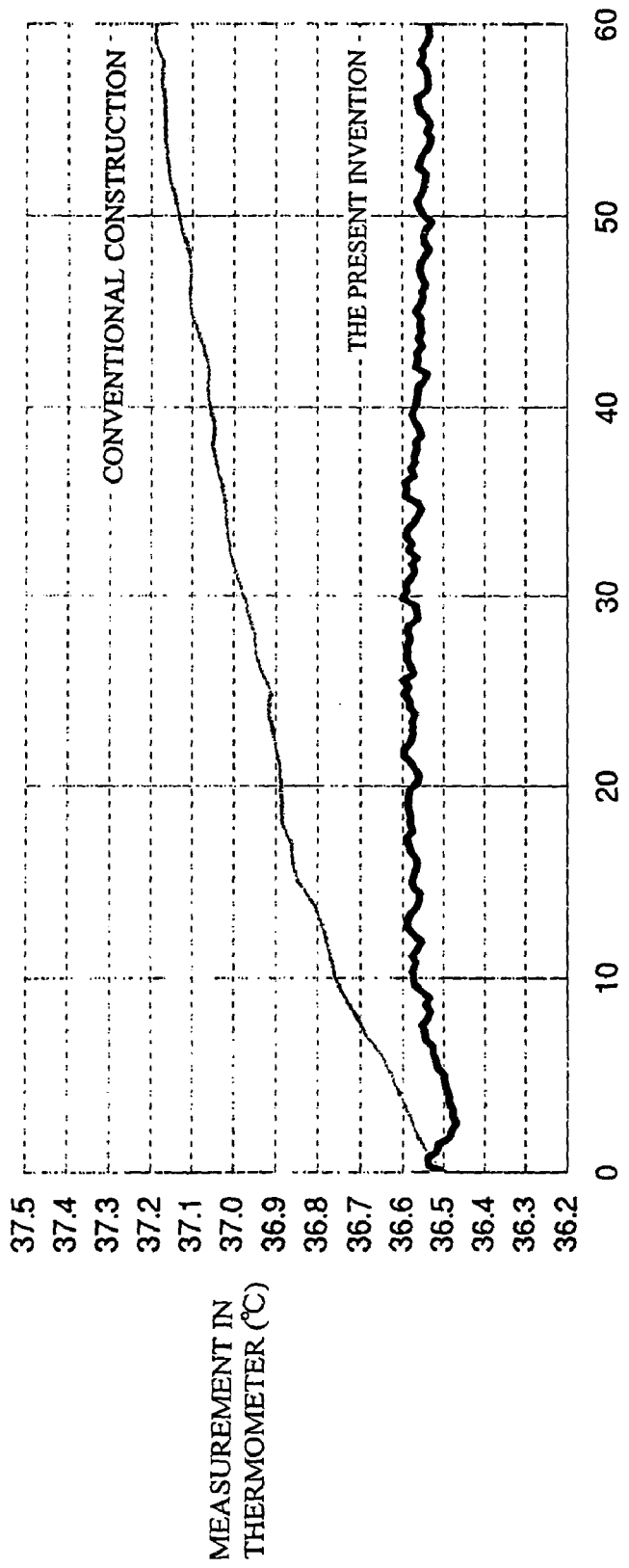
FIG. 15 is a graph showing changes of measurements in a conventional thermometer and the thermometer according to the third embodiment.

FIG. 15 shows changes of measurements in a minute after insertion into an ear for the thermometer 110 according to the embodiment, which calculates a body temperature in the above manner, and a thermometer of the conventional construction. In this manner, with the thermometer according to the embodiment, stable measurement with a very small error can be made even in the case where the probe is inserted into an ear over a long time and measurement is repeatedly made.

Figure 16:
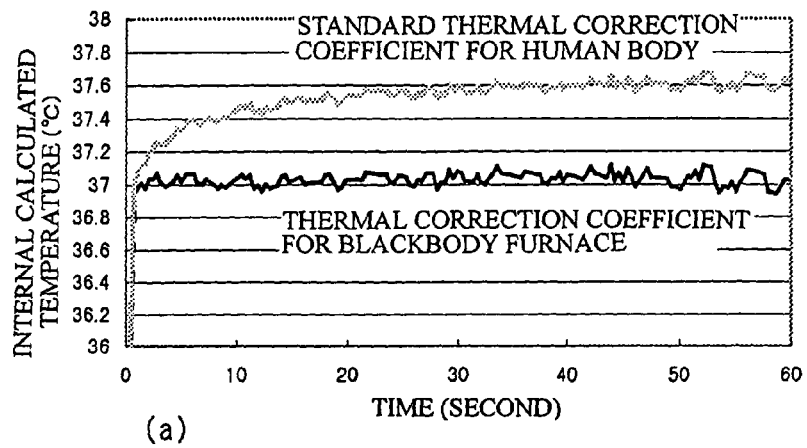
FIG. 16(a) is a graph showing data of temperature taken in a blackbody furnace relating to the thermometer according to the third embodiment.
FIG. 16(b) is a graph showing data obtained when measurement is made on a human body as an object.
FIG. 16(c) is a graph showing effects produced by optimizing a thermal correction coefficient.
Figure 16:
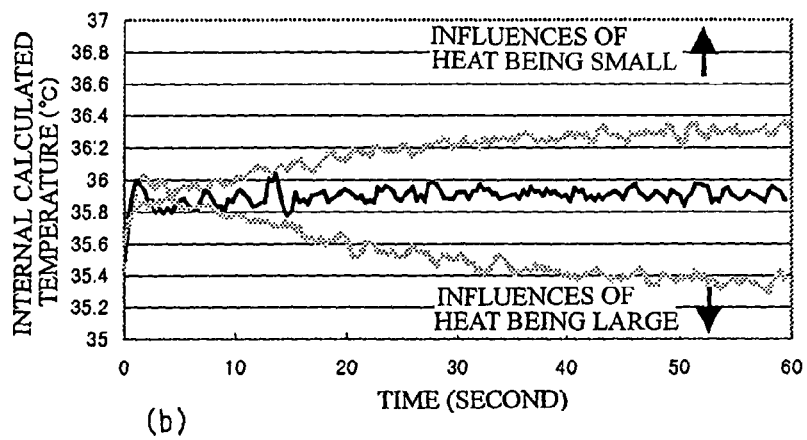
Figure 16:
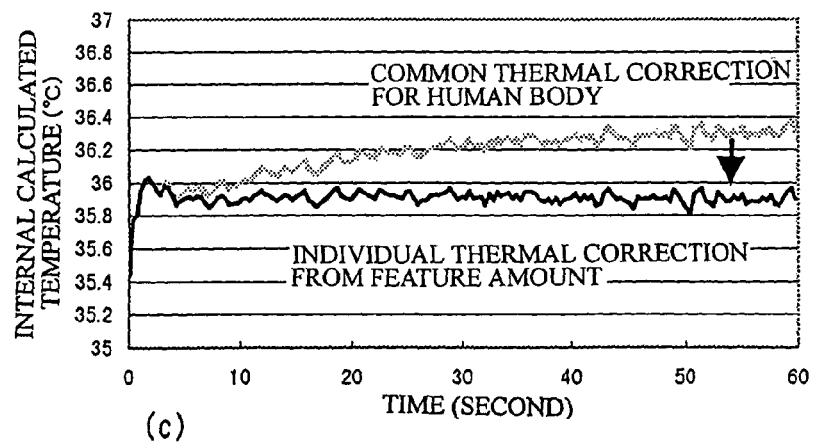

Also, FIG. 16(*a*) shows data obtained when a thermometer for calculating a temperature of an object being measured in the above manner is used to make measurement of body temperature in a blackbody furnace. An upper curve indicates temperatures calculated by means of a standard thermal correction coefficient for a human body, and a lower curve indicates temperatures calculated by means of a thermal correction coefficient for a blackbody furnace. Also, FIG. 16(*b*) shows data obtained when measurement is made on a human body as an object. A central curve indicates body temperatures calculated by means of a thermal correction coefficient for persons having standard influences of heat from an external ear, and upper and lower curves indicate the case where a standard thermal correction coefficient is used to measure persons having small and large influences of heat. Also, in FIG. 16(*c*), an upper curve indicates body temperatures of a particular person calculated by means of a standard thermal correction coefficient for a human body, and a lower curve indicates body temperatures of the particular person calculated by means of that thermal correction coefficient, which is optimized according to an individual feature amount.

By sampling temperatures of the integrated thermistor 57 continuously after power is turned on as in the embodiment, it is possible to continuously presume temperatures of respective members of the probe 4 on the basis of thermal time constants of the respective members, and to provide a thermometer involving a very small error by correction conformed to temperature differences among the respective members constituting the thermopile chip 55 and the probe 4, even when the probe 4 is inserted into an ear over a long time, and measurement is repeatedly made. When respective temperature distributions of the members constituting the probe 4 can be presumed, it is possible to measure a body temperature further correctly. However, in view of a heat flow to the thermopile chip 55 from an external heat source, a temperature of a region most suitable for correcting temperature differences between the thermopile chip 55 and the respective members of the probe 4 is made a representative temperature to perform calculation whereby a sufficiently correct high-speed measurement of body temperature is made possible.

As described above, the use of only temperature information of one integrated thermistor 57 makes it possible to eliminate influences of relative errors of a plurality of thermistors. Also, the sampling interval of A/D conversion in the integrated thermistor 57 is made smaller than thermal time constants of the respective members constituting the probe 4 whereby it is possible to precisely grasp heat flow. Also, by using the difference information for a phase lead information with respect to a measured temperature of the integrated thermistor 57 and using the weighted mean for a phase lag component, measurement of body temperature is made possible without making an arithmetic processing complex. By applying the weighted mean on difference values, it is possible to obtain temperature information of the respective members conformed further to normal thermal time constants.

Radiation thermometers including an ear type thermometer are limited in size of a probe according to applications, and so it is difficult in many cases to provide a temperature sensor, such as thermistors or the like, in a position where heat flow information from an outer wall of a probe can be obtained precisely. Even when such space can be provided, the number of temperature sensors is increased and the number of channels for A/D conversion is increased to be responsible for an increase in cost, but by extracting a feature amount of an object being measured by means of an output of the integrated thermistor 57, it is possible to avoid positional limitations and to further suppress an increase in cost.

In the embodiment and other embodiments described later, it is desired that kinds of an object being measured, distinguished on the basis of a feature amount of the object being measured be beforehand limited to several kinds such as an adult, a child, or a blackbody furnace. Since it is difficult to distinguish an object being measured, fully outside of assumption on the basis of only temperature information. Nevertheless, there is no doubt that an object being measured is not limited to these kinds.

(Fourth Embodiment)

An explanation will be given below to a fourth embodiment of the invention.

An ear type thermometer according to the embodiment is the same as the thermometer 110 according to the third embodiment. The same constituents as those of the thermometer 110 are denoted by the same reference characters, and an explanation therefor will be omitted.

The thermometer of this embodiment detects insertion of a probe 4 into an ear, and temperature information of an integrated thermistor 57, respective constituent members of the probe 4, and a thermopile chip 55 when such insertion is detected is made an initial value, and changes from the initial value are used to continuously correct an output of the thermopile chip 55.

Figure 17:
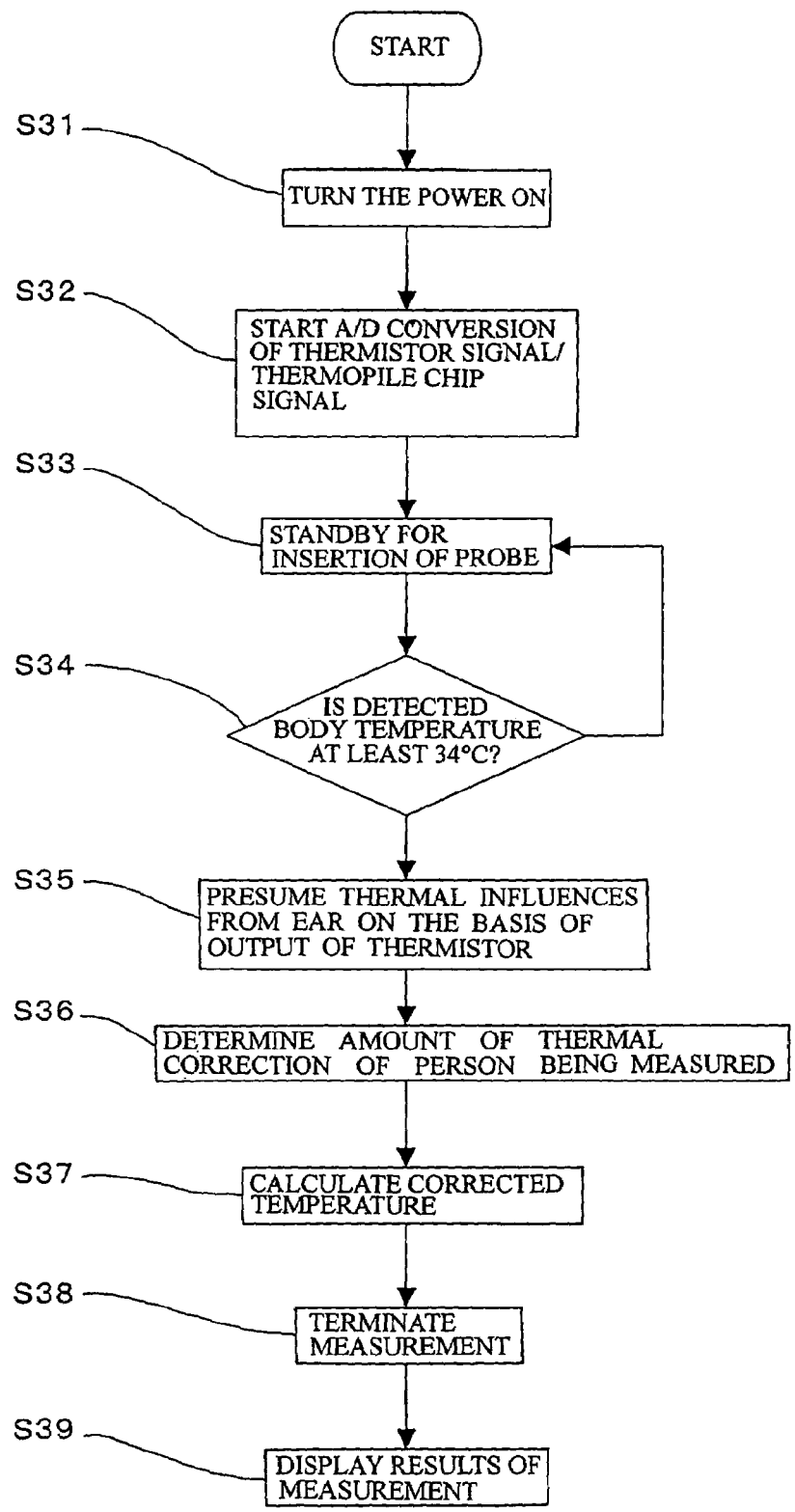
FIG. 17 is a flowchart showing the procedure of measurement of body temperature performed by an ear type thermometer according to a fourth embodiment.

FIG. 17 shows the procedure of measurement of body temperature performed by the thermometer.

First, when power is turned on (STEP 31), A/D conversion of a signal from the thermistor 57 and a signal from the thermopile chip 55 is started (STEP 32). Subsequently, insertion of the probe 4 into an ear is waited for (STEP 33). Depending upon whether a value of detected body temperature becomes at least 34° C., it is determined whether the probe 4 is inserted into an ear (STEP 34). In the case where the value of detected body temperature becomes at least 34° C., it is assumed that the probe 4 has been inserted into an ear, and the CPU 104 presumes thermal influences from an ear and an object being measured, on the basis of an output of the integrated thermistor 57 (STEP 35) to determine an amount of thermal correction corresponding to the object being measured (STEP 36). A corrected temperature is calculated on the basis of the determined amount of thermal correction (STEP 37), measurement is terminated (STEP 38), and results of measurement are displayed on a display unit 105 (STEP 39).

Here, calculation is made where T10, T20, T30 indicate values in the arithmetic expression represented in the third embodiment at the time of detecting the insertion into the ear, and correction amount of heat are assumed to be proportional to (T1−T10), (T2−T20), and (T3−T30). For example, $$\alpha(T1-T3)=T3(n)-T3(n-2)$$

makes $$\alpha\{(T1-T10)-(T3-T30)\}=T3(n)-T3(n-2)$$

Actually, the probe 4 begins to vary in temperature because of touch on the probe 4, exposure of the probe 4 to the wind, or the like before a user inserts the probe 4 into an ear. Accordingly, in the case where correction of temperature information having a long thermal time constant is made by means of weighted mean, an offset estimate of the error will remain. In order to cancel such offset error, it suffices that only changes from an initial value be used for correction where the initial value is given by information when insertion of the probe 4 into an ear is detected or measurement is started is made.

(Fifth Embodiment)

An explanation will be given below to a fifth embodiment of the invention.

An ear type thermometer 112 according to the embodiment comprises three thermistors 12, 13, 14 in addition to an integrated thermistor 57.

The thermometer 112 is constructed in the same manner as the thermometer 100 according to the second embodiment except that the three thermistors 12, 13, 14 are provided in addition to the integrated thermistor 57, and so the same reference characters are used, an explanation therefor being omitted.

Figure 18:
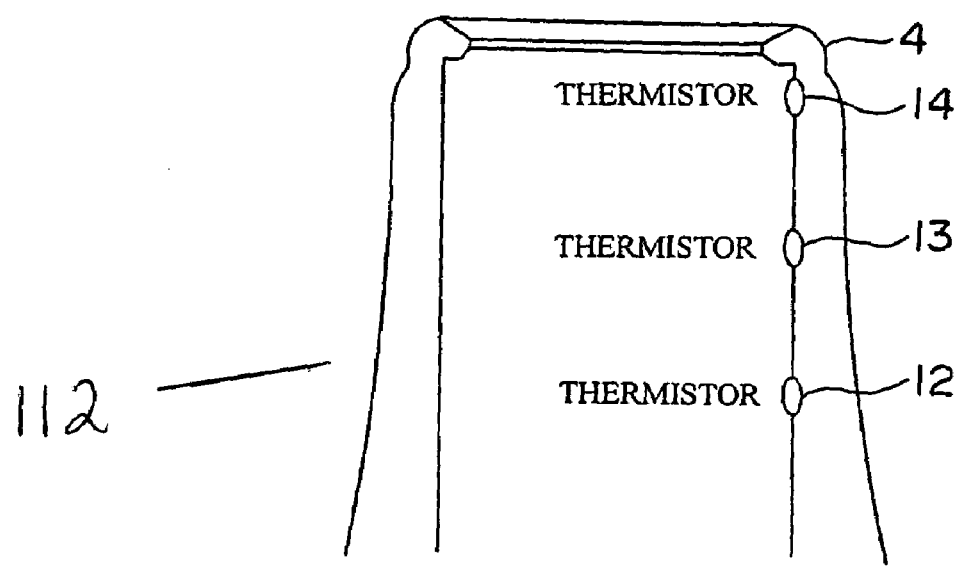
FIG. 18 is a view showing an arrangement of thermistors.

FIG. 18 schematically shows an arrangement of the three thermistors.

The thermistors 12, 13, 14 are arranged in this order from a root (base) side of the probe 4. Outputs of the thermistors 12, 13, 14 are different between the case where only a short portion on a tip end side of the probe 4 is inserted into an earhole when a person being measured is a child and the case where a portion up to a base side of the probe 4 is inserted into an earhole when a person being measured is an adult. Accordingly, outputs of the thermistors 12, 13, 14 make it possible to detect a feature amount of an object being measured, that is, how far the probe 4 is inserted, and to what extent influences of heat from outside are generated, and so it is possible on the basis of the results of detection to distinguish whether a person being measured is an adult or a child, whether an earhole is large or small, or deep or shallow.

Figure 19:
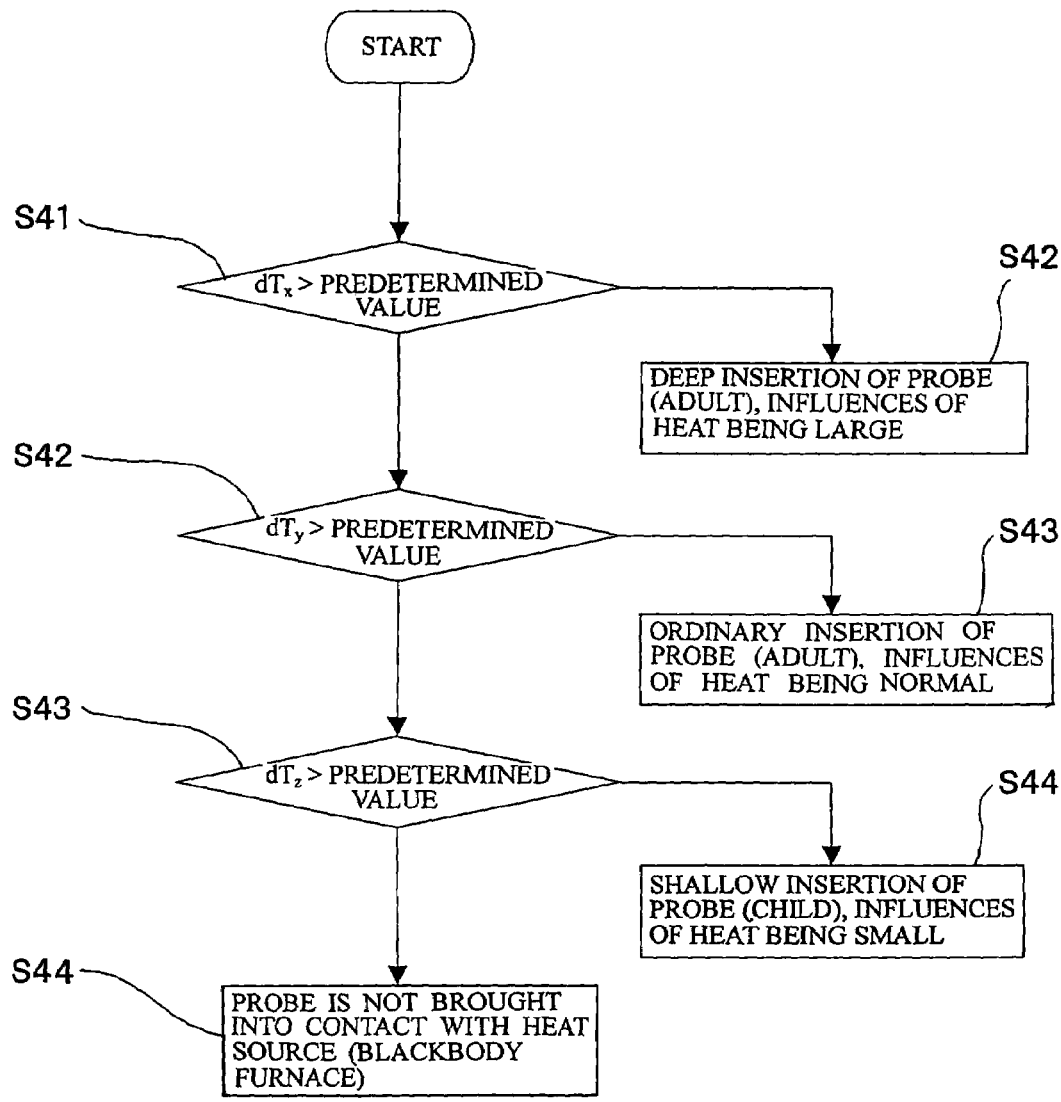
FIG. 19 is a flowchart showing the procedure of detection of a feature amount or the like of an ear type thermometer according to a fifth embodiment.

FIG. 19 shows the procedure of detection of a feature amount of an object being measured and the distinguishing procedure of the object being measured in the thermometer 112.

First, $T_x$, $T_y$, $T_z$ indicate outputs of the thermistors 12, 13, 14, respectively.

It is determined whether $dT_x$ (changed portion of $T_x$ per unit time) is greater than a predetermined value (STEP 41). When $dT_x$ is equal to or greater than the predetermined value, it is judged that the probe 4 is inserted deep and much influenced by heat, and it is presumed that a person being measured is an adult (STEP 42). Meanwhile, when $dT_x$ is less than the predetermined value, it is determined whether $dT_y$ is greater than a predetermined value (STEP 43). Here, when $dT_y$ (changed portion of $T_y$ per unit time) is equal to or greater than the predetermined value, it is judged that the probe 4 is inserted an ordinary depth and ordinarily influenced by heat, and it is presumed that a person being measured is an adult (STEP 44). Meanwhile, when $dT_y$ is less than the predetermined value, it is determined whether $dT_z$ (changed portion of $T_z$ per unit time) is greater than a predetermined value (STEP 45). Here, when $dT_z$ is equal to or greater than the predetermined value, it is judged that the probe 4 is inserted only shallow and slightly influenced by heat, and it is presumed that a person being measured is a child (STEP 46). Meanwhile, when $dT_z$ is less than the predetermined value, it is judged that the probe is not brought into contact with a heat source, and it is presumed that an object being measured is a blackbody furnace (STEP 47).

Since the procedure of measurement of body temperature performed by the thermometer 112 according to the embodiment is the same as that by the thermometer 110, shown in FIG. 12, according to the third embodiment, an explanation therefor will be omitted.

Here, while three thermistors for distinguishing a feature of an object being measured are arranged in addition to an integrated thermistor, the number of thermistors is not limited to three.

Figure 20:
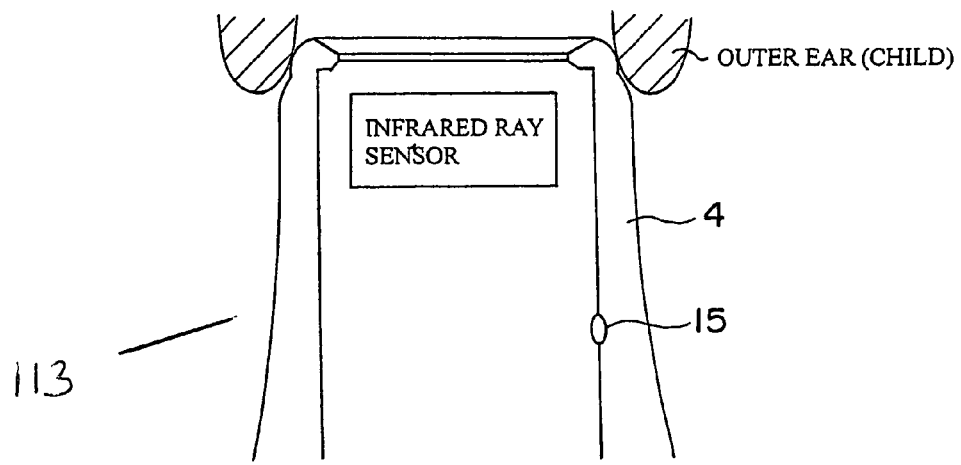
FIGS. 20(a) and 20(b) are views showing other arrangements of a thermistor.
Figure 20:
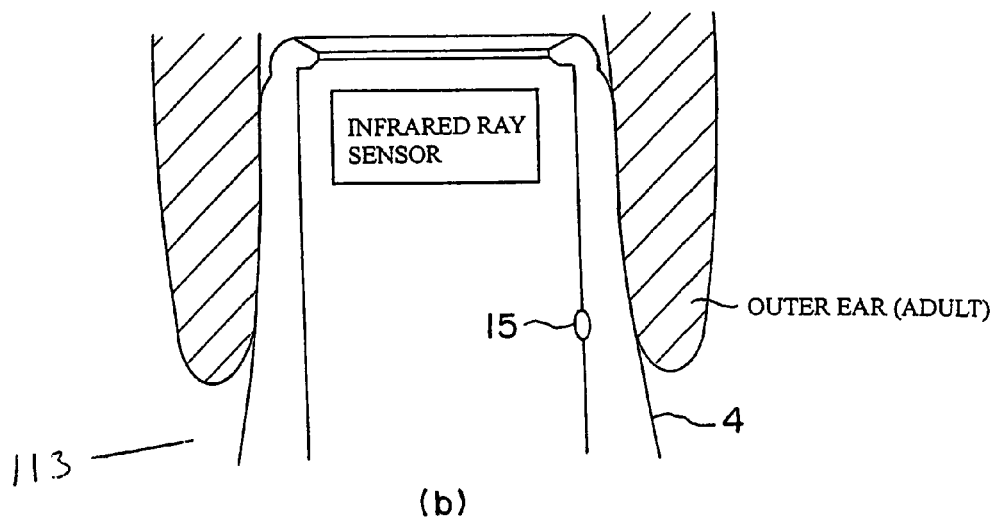

As shown in FIG. 20, a thermistor 15 may be arranged in a position on a side of a base of the probe 4 distant from a tip end of the probe. Thus an output of the thermistor 15 arranged in a position distant from the tip end of the probe 4 also makes it possible to detect whether the probe 4 is inserted shallow into an earhole (FIG. 20(a)) in the case where a person being measured is a child, and whether the probe 4 is inserted shallow into an earhole (FIG. 20(b)), so that an object being measured can be distinguished on the basis of results of the detection. Since an internal constitution of the thermometer 113 thus constructed is the same as that shown in FIG. 8 except that only one thermistor is provided, an explanation therefor will be omitted.

Figure 21:
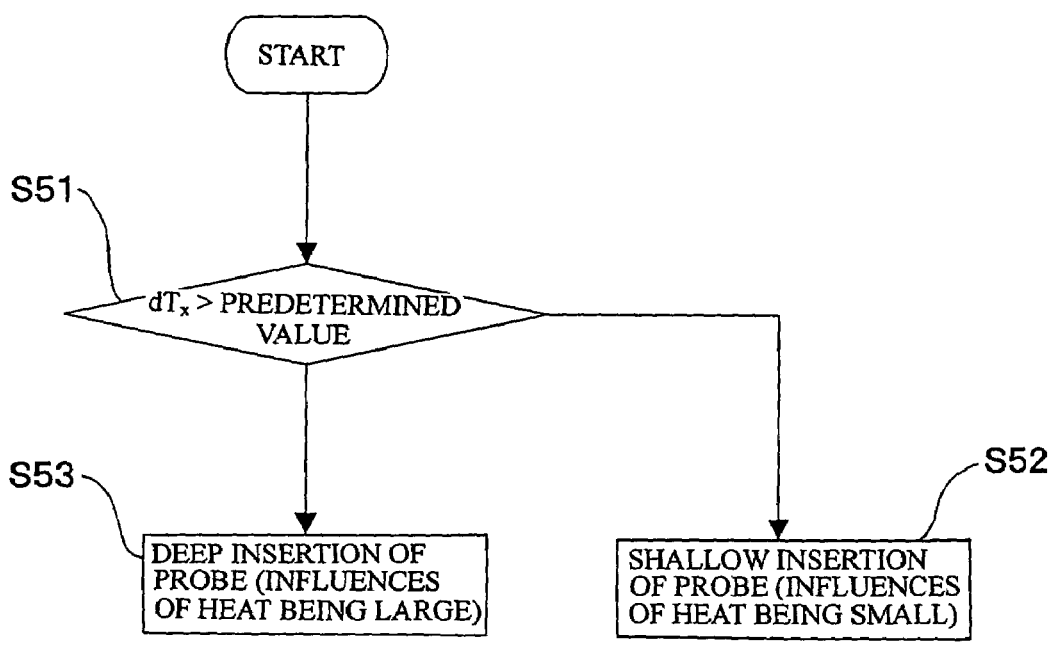
FIG. 21 is a flowchart showing the procedure of detection of a feature amount or the like of another ear type thermometer according to the fifth embodiment.

FIG. 21 shows the procedure of detection of a feature amount of an object being measured and the distinguishing procedure of the object being measured, with the use of the thermistor 15. Since measurement of body temperature with the thermometer 113 is performed in the same manner as in the procedure shown in FIG. 12, an explanation therefor will be omitted.

Here, where $T_x$ indicates an output of a thermistor 14, it is determined whether a changed portion $dT_x$ per unit time is greater than a predetermined value (STEP 51). When $dT_x$ is equal to or less than the predetermined value, it is judged that the probe 4 is inserted only shallow and slightly influenced by heat (here, it can be presumed that a person being measured is a child) (STEP 52). Meanwhile, when $dT_x$ is greater than the predetermined value, it is judged that the probe 4 is inserted deep and much influenced by heat (here, it can be presumed that a person being measured is an adult) (STEP 53).

Here, in place of $dT_x$, $T_a$ indicates a temperature of the probe 4 before insertion into an ear, and then the judgment condition in STEP 31 can be made $\{dT_x/(T_x-T_a)\}$>(predetermined value)

Ordinarily, since the greater a temperature difference between an environmental temperature and a temperature of an ear, the greater $dT_x$, influences caused by the environmental temperature can preferably be eliminated by normalization with a temperature difference between an environmental temperature and a temperature of an ear. The judgment conditions in the above STEPs 11, 13, 15 can be set in the same manner as above.

In this manner, with only one thermometer, detection of a feature amount of an object being measured and distinguishment of the object being measured can be made.

(Sixth Embodiment)

An explanation will be given below to a sixth embodiment of the invention.

An internal constitution of an ear type thermometer 114 according to the embodiment is the same as that of the thermometer 100 shown in FIG. 8 except that a substrate jumper switch 150 is provided. The same reference characters are used for the same constituents, and an explanation therefor will be omitted.

Figure 22:
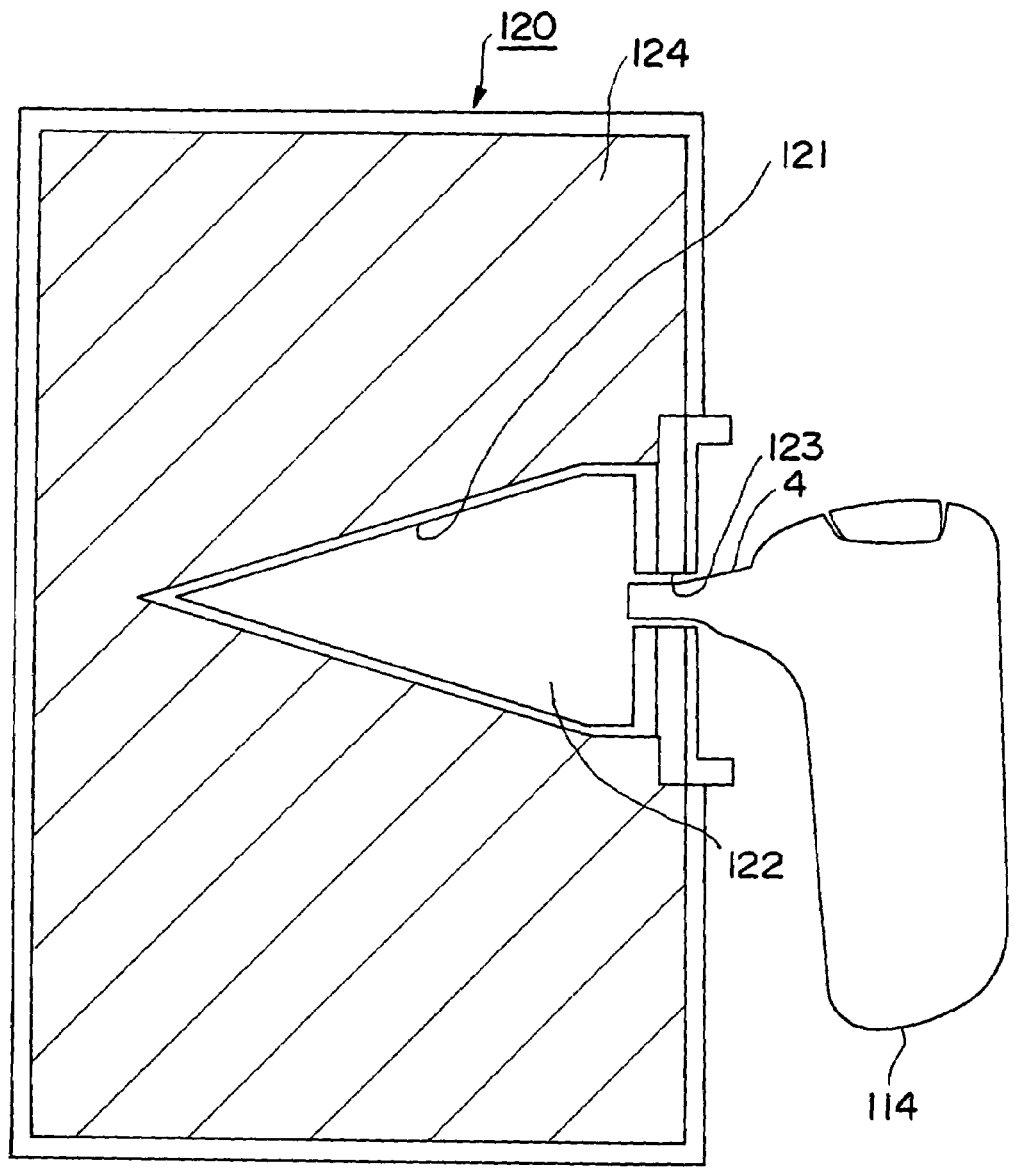
FIG. 22 is a view illustrating a state, in which a blackbody furnace is used.

Here, an explanation will be given to a blackbody furnace. FIG. 22 schematically shows a state, in which a blackbody furnace 120 is used. The blackbody furnace 120 is used for examining the accuracy of a thermometer or calibrating measurements as described later. The blackbody furnace 120 has a cavity 122, of which inner wall surface 121 is subjected to surface blackbody coating, and when a probe 4 of the thermometer 114 is inserted through an insertion hole 123, an opening on a tip end of the probe fronts on an interior of the cavity. The cavity 122 is surrounded by a constant temperature bath 124, which is maintained at a constant temperature by a heater (not shown). Thermal radiation incident on the cavity 122 from the insertion hole 123 is completely absorbed, and the cavity 122 is filled with blackbody radiation.

Figure 23:
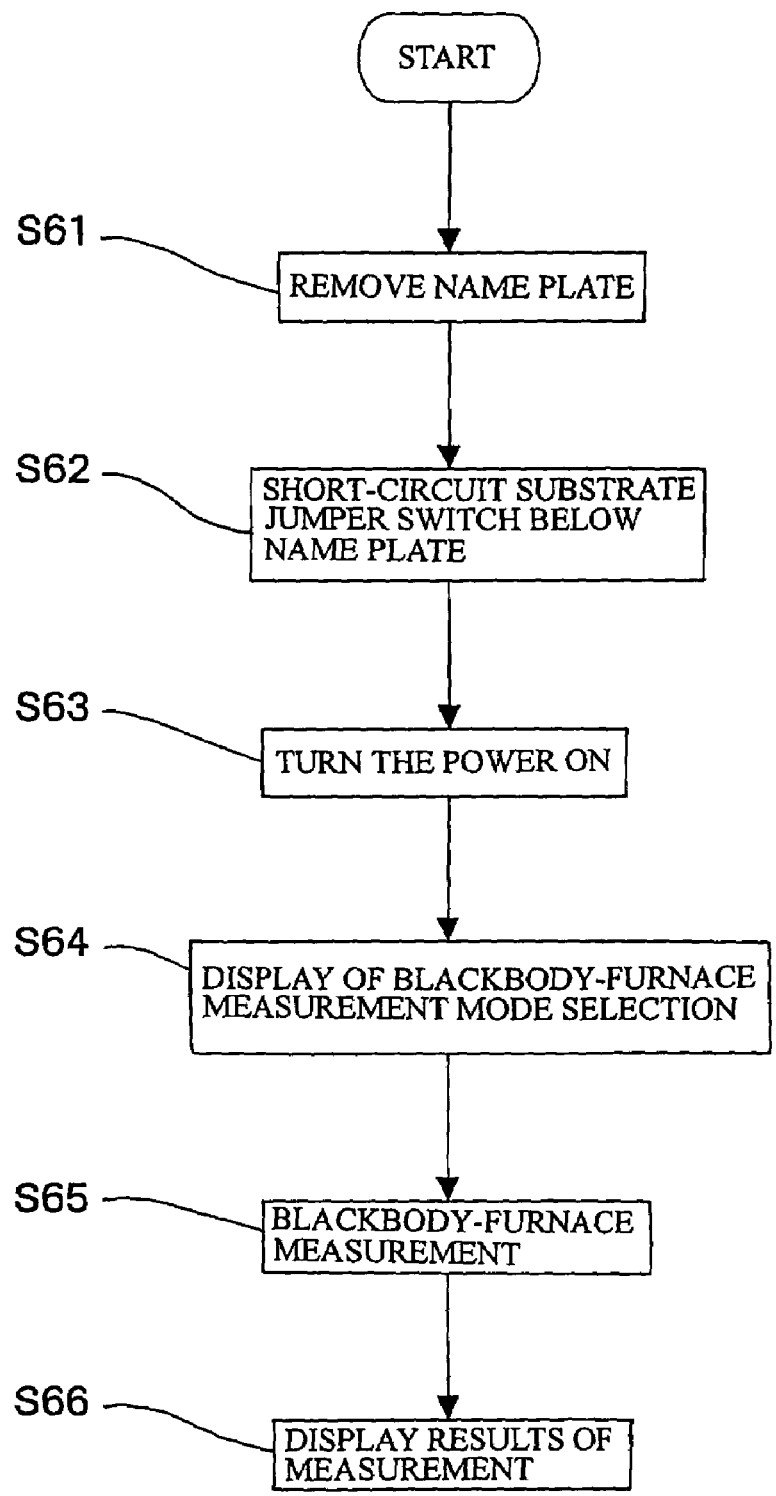
FIG. 23 is a flowchart showing the procedure of measurement in a blackbody-furnace measurement mode.
Figure 24:
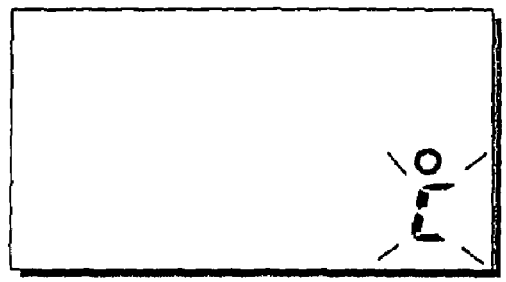
FIGS. 24(a) and 24(b) are views illustrating display examples of a display unit in the blackbody-furnace measurement mode.
Figure 24:
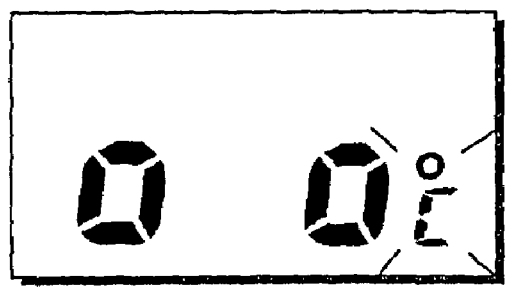

The thermometer 114 according to the embodiment comprises a mode, in which the above blackbody furnace 120 is used to prove the accuracy of measurement. FIG. 23 shows the procedure of measurement in such blackbody-furnace measurement mode. First, a person in charge of examination first removes a nameplate of the thermometer 114 (STEP 61). Provided below the nameplate of the thermometer 114 is the substrate jumper switch 150, which is short-circuited by the person in charge of examination (STEP 62). The person in charge of examination turns on the power in this state (STEP 63). At this time, a display unit 105 displays a specific measurement standby state (FIG. 24(b)) when the blackbody-furnace measurement mode is selected, different from a normal measurement standby state (FIG. 24(a)) (STEP 64). Having checked by way of the display on the display unit 105 that the blackbody-furnace measurement mode is selected, the person in charge of examination inserts the probe 4 into the insertion hole 123 of the blackbody furnace 120, and a predetermined procedure of measurement is made (STEP 65). When the measurement is terminated, results of measurement are displayed on the display unit 105 and so the procedure in the blackbody-furnace measurement mode is terminated (STEP 66). Here, actions in STEPs 61 to 63 are made by the person in charge of examination, and STEP 64 and the following represent processings in the thermometer 114.

In this manner, in the case of enabling selection of the measurement mode, in which the blackbody furnace 120 is used for proof of accuracy, it is possible to make data processing, such as correction or the like, in view of influences of heat generated when a blackbody furnace is used, so that proof of accuracy can be correctly made.

Also, clinical offset is in some cases set in an ear type thermometer as desired on the basis of a difference between a blackbody (emissivity=1) and a human body (emissivity≠1) when a human body is to be measured. However, when a blackbody is measured in a state, in which such clinical offset is set, it is difficult to determine whether results of temperature taken are correct, except for a strictly controlled state. Accordingly, when the blackbody-furnace measurement mode is provided as in the embodiment, it is possible to correctly examine results of temperature taken.

Figure 25:
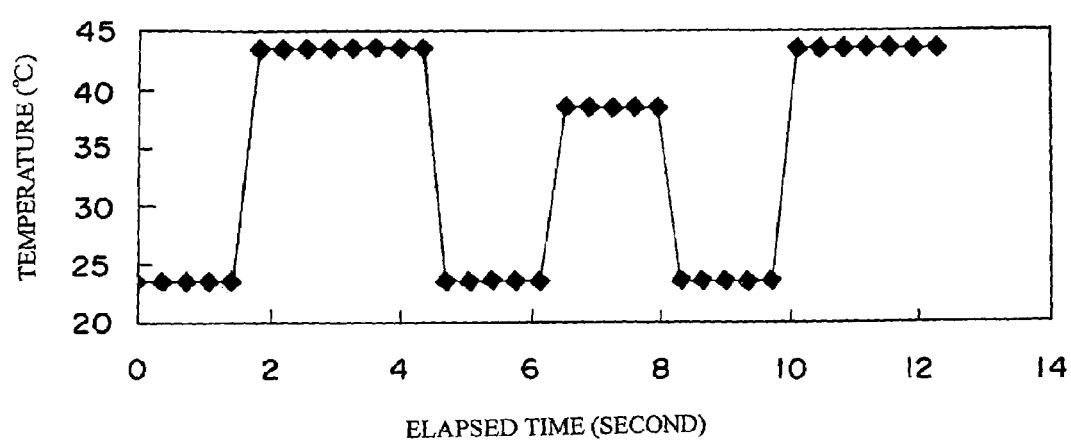
FIG. 25 is a graph showing a pattern of changes in radiation temperature for transition to the blackbody-furnace measurement mode.

While a switch for selection of the blackbody-furnace measurement mode is provided in the embodiment, a temperature pattern, as shown in FIG. 25, which is ordinarily hard to occur, may be beforehand set and may be set to the blackbody-furnace measurement mode in the case where such temperature pattern is detected after power is turned on. With such arrangement, there is no need of disassembling a thermometer for the purpose of selecting the blackbody-furnace measurement mode, and such situation is eliminated, in which setting of the blackbody measurement mode is set at an unexpected occasion and measurement of body temperature cannot be made correctly.

(Seventh Embodiment)

An explanation will be given below to a seventh embodiment of the invention.

An ear type thermometer 115 according to the embodiment is a device capable of making measurement with the use of the above blackbody furnace 120. For example, a thermometer capable of selecting the blackbody-furnace measurement mode with the use of a switch or the like, like the thermometer 114 according to the sixth embodiment will do, but the present thermometer is not limited thereto.

The ear type thermometer 115, for example, can be constructed by providing informing means on the thermometer 114. Here, such informing means may be one for visually making information through the display unit 105, LED, or the like, or one for audibly making information through buzzer, or the like, and may be one capable of giving information to a user through the five senses.

Figure 26:
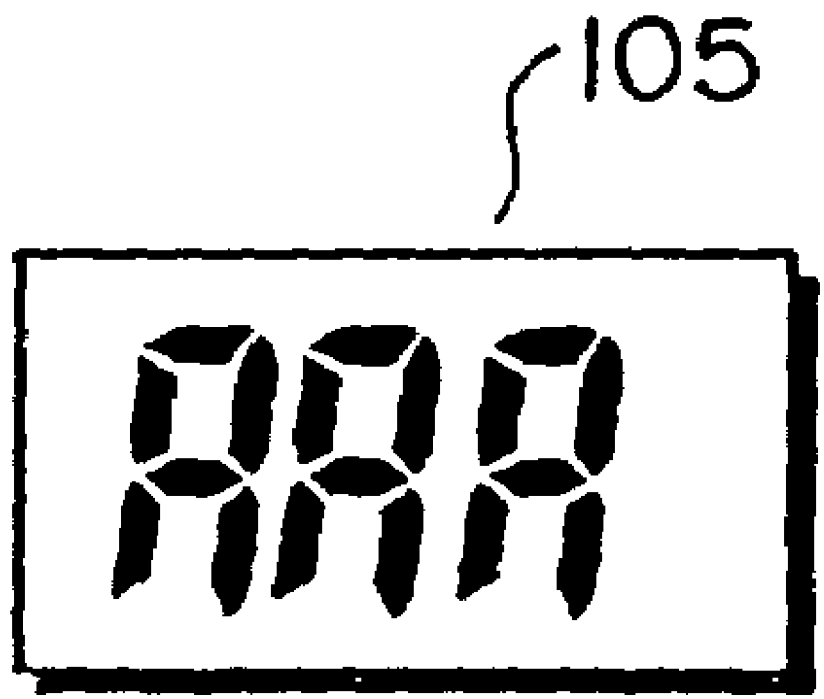
FIG. 26 is a view showing a display example of an alarm in the blackbody-furnace measurement mode.
Figure 27:
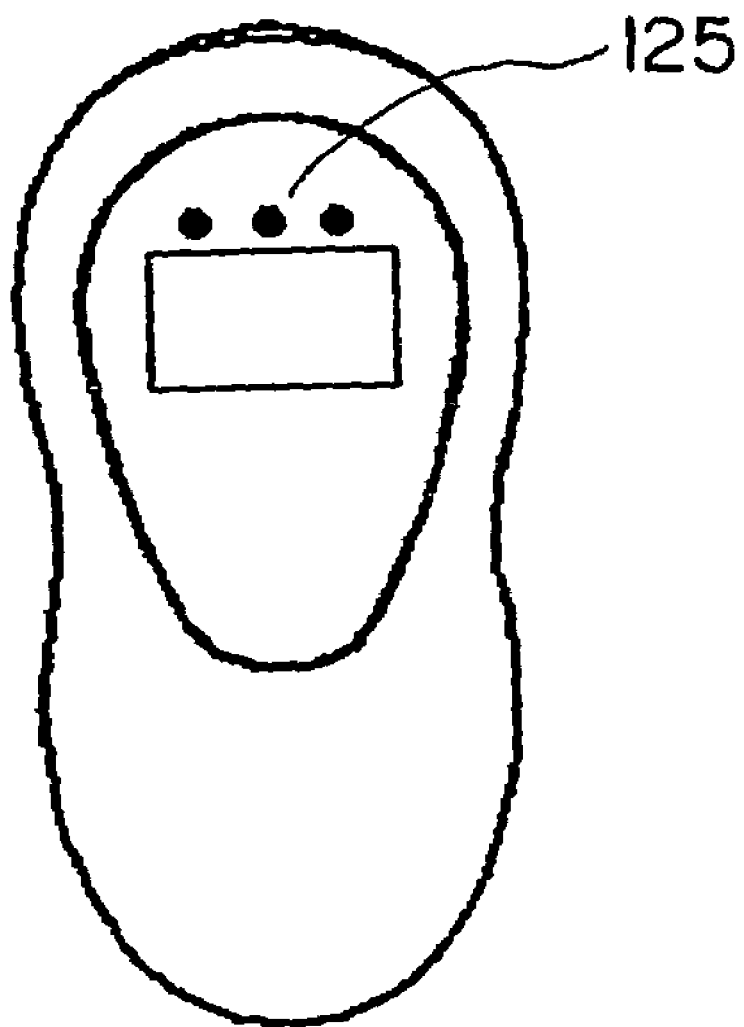
FIG. 27 is a view showing another display example of an alarm in the blackbody-furnace measurement mode.

Radiation thermometers cause measurement errors on principles in a state, in which thermal balance is lost. Accordingly, it is also necessary in the ear type thermometer 115 as in the embodiment to ordinarily make measurement in a state, in which the thermometer is adjusted to a measurement environment over a predetermined period of time to be made thermally stable. In the case where operations for adjustment and proof of accuracy are performed in the blackbody-furnace measurement mode, they must also be performed in a controlled condition because generation of errors is caused when measurement is made before a thermometer becomes thermally stable. Therefore, $T_b$ detected by the integrated thermistor 57 is used in the thermometer 115 at the time of blackbody-furnace measurement, and an alarm display such as "AAA", or the like as shown in FIG. 26 is displayed on an LCD of the display unit 105 in the case where the absolute value of $T_b$ is at least a predetermined value. Also, an LED 125 may be turned on or flashed as shown in FIG. 27. Thus a person in charge of examination can recognize adjustment and temperature-measuring in a thermally unstable state, so that it is possible to avoid operations in such state.

(Eighth Embodiment)

An explanation will be given below to an eighth embodiment of the invention.

An ear type thermometer 116 according to the embodiment is a device capable of making measurement with the use of the blackbody furnace 120 in the same manner as the sixth embodiment. This embodiment can be configured in the same manner as the sixth embodiment or other embodiments, in which measurement is possible with the use of a blackbody furnace, except the constitution of a display unit 105.

The thermometer 116 has the display resolution of the display unit 105 increasing one place in the case where operations such as proof of accuracy, or the like are performed with the use of a blackbody furnace.

Figure 28:
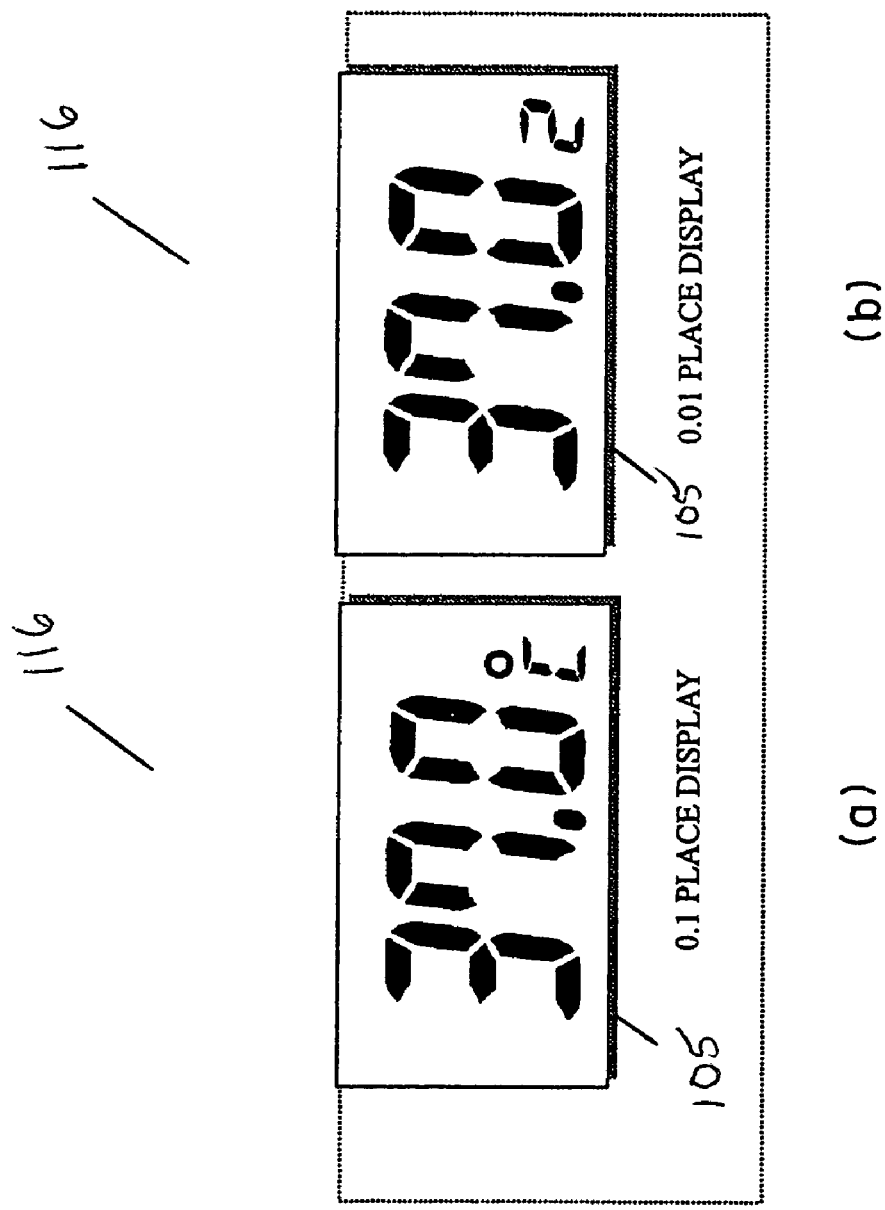
FIGS. 28(a) and 28(b) are views showing display examples for a figure of 0.1 place and for a figure of 0.01 place.

Generally, with thermometers, places of insured temperatures are in many cases consistent in places of display temperatures, and ear type thermometers involve an insured accuracy of ±0.1° C., a display resolution of ±0.1° C., or the like. In the case where a blackbody furnace is used to perform examination of accuracy, or the like, however, display in a higher display resolution is desirable in order to control scattering of actual values, measurements, or the like. In view of this, the display unit 105 composed of LCD is configured in the thermometer 116 as shown in FIG. 28. More specifically, ordinarily or at the time of the blackbody-furnace measurement mode (for a 0.1 place), 0.1 place display is made as shown in FIG. 28(a), in which rightmost segments indicate a temperature unit "° C.". With the thermometer 116, rightmost segments are also composed from seven segments in the same manner as left figures such that at the time of blackbody-furnace measurement in the blackbody-furnace measurement mode (for a 0.01 place), 0.01 place display is made as shown in FIG. 28(b) and right most segments are able to display a digit in a 0.01 place.

Figure 29:
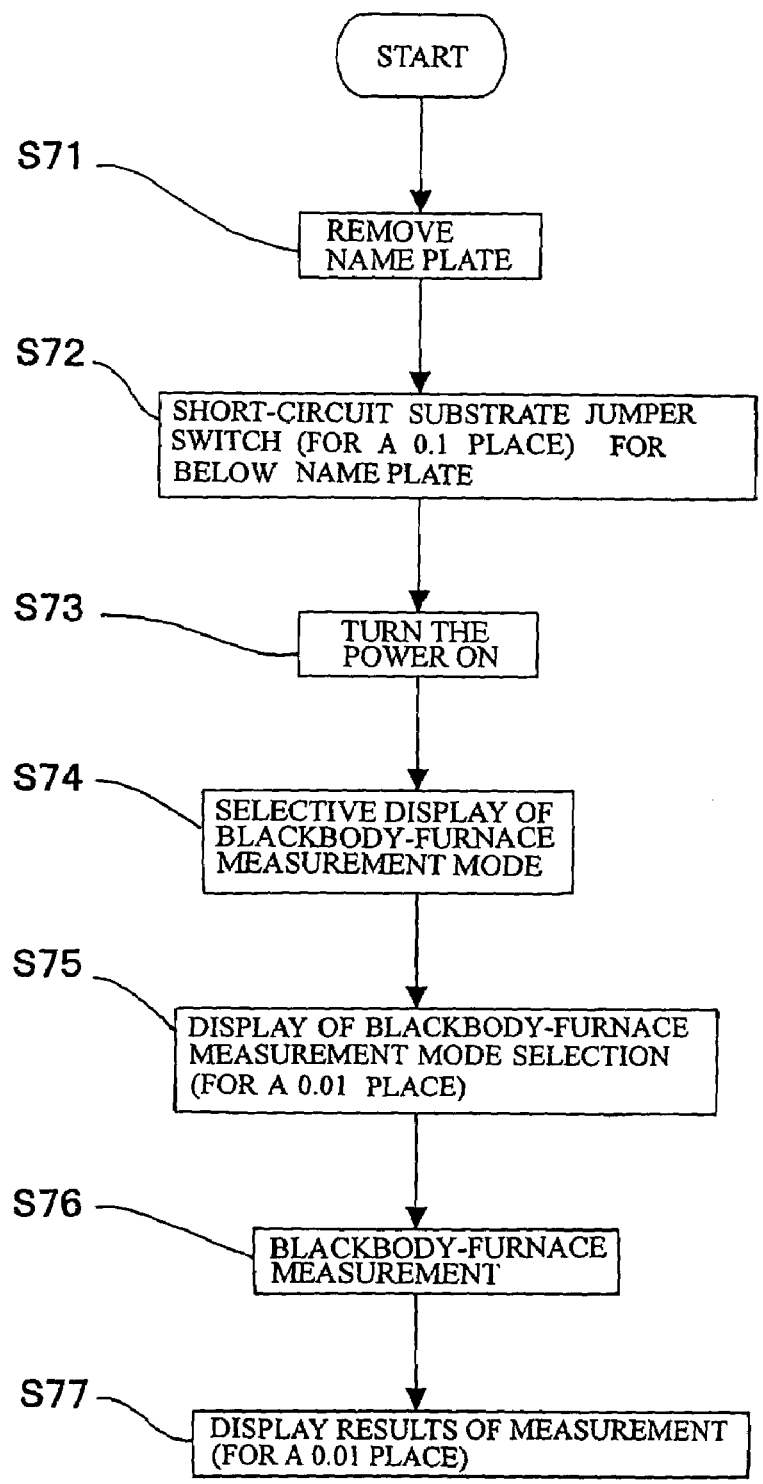
FIG. 29 is a flowchart showing the procedure of measurement in the blackbody-furnace measurement mode in the case of display in a figure of 0.01 place.

FIG. 29 shows the procedure in the case where blackbody-furnace measurement is made with 0.01 place display in. Since the procedure of processings is substantially the same as in the case of a normal blackbody-furnace measurement for a 0.1 place shown in FIG. 23, an explanation will be given only to different portions.

Here, after a nameplate is removed, a substrate jumper switch for a 0.01 place is short-circuited (STEP 72). Also, after power is turned on, selection of the blackbody-furnace measurement mode is displayed with 0.1 place display as shown in FIG. 28(a) (STEP 74). Thereafter, displaying of temperature unit disappears as shown in FIG. 28(b), selection of the blackbody-furnace measurement mode for a 0.01 place is displayed, and results of measurement including a digit of 0.01 place are displayed (STEP 77).

In this manner, by increasing one figure in display resolution at the time of blackbody-furnace measurement, examination can be strictly made and control of examination data is also made possible. Also, by using a normal display portion for temperature unit and a display portion for increased figures in common, there is no need of increasing the number of segments in LCD and decreasing places in temperature display. While a rightmost numeral becomes small, there is caused no problem since it is not used by a general user. Also, the temperature unit and numeral may be alternately displayed. Further, the display resolution at the time of blackbody-furnace measurement may increase two or more places. Also, while "° C." is displayed as a temperature unit, the same is with the case where "° F." is displayed.

INDUSTRIAL APPLICABILITY

As described above, it has been possible according to the invention to suppress measurement errors caused by influences of heat from outside to enhance accuracy in temperature measurement.

The invention claimed is:

1. A radiation thermometer, comprising:
an infrared-ray sensor for measuring a quantity of infrared rays irradiated from an object being measured,
sensor-temperature measuring unit to measure a temperature of the infrared-ray sensor,
a probe receiving therein the infrared-ray sensor and the sensor-temperature measuring unit and said probe is inserted into an opening, and
temperature calculating unit to calculate a temperature of the object being measured, on the basis of a quantity of infrared rays irradiated from the object being measured, and a temperature of the infrared-ray sensor;
said temperature calculating unit comprising representative temperature presuming unit to presume a temperature of the infrared-ray sensor or information of a temperature representative of any one of members constituting the probe in conformity to thermal time constants peculiar to the respective members from heat conducted to the infrared-ray sensor and the members by a heat source in the vicinity of an outer wall of the probe; and a temperature difference information presuming unit to calculate at least either of a phase lead component or a phase lag component of results of measurement of the sensor-temperature measuring unit in conformity to thermal time constants of the members present on a heat conduction path passing through the sensor-temperature measuring unit to presume a temperature difference information between the sensor-temperature measuring unit and the infrared-ray sensor and the members.

2. The radiation thermometer according to claim 1, wherein information including a difference of results of measurement of the sensor-temperature measuring unit as the phase lead component and information including a weighted mean of results of measurement of the sensor-temperature measuring unit as the phase lag component is calculated.

3. The radiation thermometer according to claim 1 or 2, further comprising infrared-ray output correcting unit to correct results of measurement by the infrared-ray sensor continuously from the time of turning on the power on the basis of temperature difference information presumed by the temperature difference information presuming unit.

4. The radiation thermometer according to claim 3, wherein the infrared-ray output correcting unit has the function of correcting results of measurement by the infrared-ray sensor on the basis of changes of that temperature difference information, which is presumed by the temperature difference information presuming unit, since the start of measurement of a radiation temperature of the object being measured.

5. The radiation thermometer according to claim 3, further comprising insertion detecting unit to detect insertion of the probe into the opening, and
wherein the infrared-ray output correcting unit has the function of correcting results of measurement by the infrared-ray sensor on the basis of changes of temperature difference information, which is presumed by the temperature difference information presuming unit, since the time of detection of insertion by the insertion detecting unit.

6. The radiation thermometer according to any one of claims 1 to 2, further comprising infrared-ray output correcting unit to correct results of measurement by the infrared-ray sensor continuously from the time of turning on the power on the basis of a temperature presumed by the representative temperature presuming unit, wherein the infrared-ray output correcting unit has the function of correcting results of measurement by the infrared-ray sensor on the basis of changes of that temperature, which is presumed by the representative temperature presuming unit, since the start of measurement of a radiation temperature of the object being measured.

7. The radiation thermometer according to any one of claims 1 to 2, further comprising infrared-ray output correcting unit to correct results of measurement by the infrared-ray sensor continuously from the time of turning on the power on the basis of a temperature presumed by the representative temperature presuming unit, further comprising insertion detecting unit to detect insertion of the probe into the opening, and
wherein the infrared-ray output correcting unit has the function of correcting results of measurement by the infrared-ray sensor on the basis of changes of that temperatures, which is presumed by the representative temperature presuming unit, since the time of detection of insertion by the insertion detecting unit.

* * * * *

UNITED STATES PATENT AND TRADEMARK OFFICE
CERTIFICATE OF CORRECTION

| | | |
|---|---|---|
| PATENT NO. | : 7,036,978 B2 | Page 1 of 1 |
| APPLICATION NO. | : 10/311059 | |
| DATED | : May 2, 2006 | |
| INVENTOR(S) | : Makoto Tabata et al. | |

It is certified that error appears in the above-identified patent and that said Letters Patent is hereby corrected as shown below:

On Title page item 75
In the Inventors, delete "Tatsuya" and replace with --Tetsuya--

Signed and Sealed this

Twenty-third Day of January, 2007

JON W. DUDAS
*Director of the United States Patent and Trademark Office*